United States Patent [19]

Finkelstein et al.

[11] Patent Number: 5,418,250

[45] Date of Patent: * May 23, 1995

[54] IMIDAZOLYL-ALKENOIC ACIDS USEFUL AS ANGIOTENSIN II RECEPTOR ANTAGONISTS

[75] Inventors: Joseph A. Finkelstein, Philadelphia; Richard M. Keenan, Malvern; Joseph Weinstock, Phoenixville, all of Pa.

[73] Assignee: SmithKline Beecham Corporation, Philadelphia, Pa.

[*] Notice: The portion of the term of this patent subsequent to Feb. 9, 2010 has been disclaimed.

[21] Appl. No.: 76,609

[22] Filed: Jun. 14, 1993

Related U.S. Application Data

[63] Continuation of Ser. No. 954,777, Sep. 30, 1992, abandoned, which is a continuation of Ser. No. 746,262, Aug. 14, 1991, Pat. No. 5,185,351, which is a continuation-in-part of Ser. No. 629,123, Dec. 14, 1990, abandoned, which is a continuation-in-part of Ser. No. 506,412, Apr. 6, 1990, abandoned, which is a continuation-in-part of Ser. No. 366,079, Jun. 14, 1989, abandoned.

[51] Int. Cl.$^6$ .............. A61K 31/415; C07D 233/66; C07D 409/06
[52] U.S. Cl. .................... 514/397; 514/341; 548/315.1
[58] Field of Search .............. 514/397, 341; 548/315.1

[56] References Cited

U.S. PATENT DOCUMENTS

| | | | |
|---|---|---|---|
| 4,340,598 | 7/1982 | Furukawa et al. | 548/315.1 X |
| 4,355,040 | 10/1982 | Furukawa et al. | 548/315.1 X |
| 5,185,351 | 2/1993 | Finrelstein et al. | 514/341 |

FOREIGN PATENT DOCUMENTS

| | | | |
|---|---|---|---|
| 0103647 | 3/1984 | European Pat. Off. | 514/341 |
| 0218398 | 4/1987 | European Pat. Off. | 548/315.1 |
| 0253310 | 1/1988 | European Pat. Off. | 548/315.1 |
| 0324377 | 1/1989 | European Pat. Off. | 548/315.1 |
| 86/07054 | 12/1986 | WIPO | 548/315.1 |
| 87/03591 | 6/1987 | WIPO | 548/315.1 |
| 92/10482 | 6/1992 | WIPO | 548/315.1 |

OTHER PUBLICATIONS

Berger, "Medicinal Chemistry", 2nd Ed., pp. 565–571, 600, 601 (1960).
Denrewalter et al, "Progress in Drug Research", vol. 10, pp. 510–512 (1966).

*Primary Examiner*—Floyd D. Higel
*Attorney, Agent, or Firm*—Mary E. McCarthy; Stephen Venetianer; Edward T. Lentz

[57] ABSTRACT

Angiotensin II receptor antagonists having the formula:

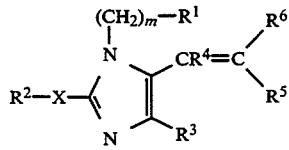

which are useful in regulating hypertension and in the treatment of congestive heart failure, renal failure, and glaucoma, pharmaceutical compositions including these antagonists, and methods of using these compounds to produce angiotensin II receptor antagonism in mammals.

7 Claims, No Drawings

IMIDAZOLYL-ALKENOIC ACIDS USEFUL AS ANGIOTENSIN II RECEPTOR ANTAGONISTS

This is a continuation of application Ser. No. 07/954,777, filed Sep. 30, 1992, now abandoned, which is a continuation of application Ser. No. 07/746,262, filed Aug. 14, 1991 now U.S. Pat. No. 5,185,351, which is a continuation-in-part of application Ser. No. 07/629,123 filed Dec. 14, 1990, now abandoned, which is a continuation-in-part of application Ser. No. 07/506,412 filed Apr. 6, 1990, now abandoned, which is a continuation-in-part of application Ser. No. 07/366,079 filed Jun. 14, 1989, now abandoned.

The present invention relates to new imidazolyl-alkenoic acids which are angiotensin II receptor antagonists and are useful in regulating hypertension induced or exacerbated by angiotensin II, and in the treatment of congestive heart failure, renal failure, and glaucoma. This invention also relates to pharmaceutical compositions containing these compounds and methods for using these compounds as antagonists of angiotensin II, as antihypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.*, 76, 612). Also, a recent patent application (South African Patent Application No. 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

Furukawa et al., U.S. Pat. No. 4,340,598 discloses imidazol-5-yl-acetic acids and imidazol-5-yl-propanoic acids. Specifically, the discloser includes 1-benzyl-2-n-butyl-5-chloroimidazole-4-acetic acid and 1-benzyl-2-phenyl-5-chloroimidazole-4-propanoic acid.

Furukawa, et al., U.S. Pat. No. 4,355,040 discloses substituted imidazole-5-acetic acid derivatives. A compound specifically disclosed is 1-(2-chlorobenzyl)-2-n-butyl-4-chloroimidazole-5-acetic acid.

Carini et al. in EP 253,310 disclose certain imidazolyl-propenoic acids. Two intermediates described in this patent are ethyl 3-[1-(4-nitrobenzyl)-2-butyl-4-chloroimidazol-5-yl]propenoate and ethyl 3-[2-butyl-4-chloro-1-(4-aminobenzyl)imidazol-5-yl]propenoate.

Also, Wareing, in PCT/EP 86/00297, discloses as intermediates certain imidazolylpropenoate compounds. On page 62, Formula (CX) is ethyl 3-[1(-4-fluorophenyl)-4-isopropyl-2-phenyl-1H-imidazol-5-yl]-2-propenoate.

DESCRIPTION OF THE INVENTION

The compounds of the present invention that are blockers of angiotensin II receptors are represented by the following Formula (I):

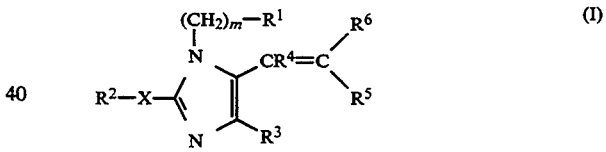

in which:

$R^1$ is adamantyl, phenyl, biphenyl, or naphthyl, with each aryl group being unsubstituted or substituted by one to three substituents selected from Cl, Br, F, I, $C_1$-$C_6$alkyl, nitro, A—$CO_2R^7$, tetrazol-5-yl, $C_1$-$C_6$alkoxy, hydroxy, $SC_1$-$C_6$alkyl, $SO_2NHR^7$, $NHSO_2R^7$, $SO_3H$, $CONR^7R^7$, $CN$, $SO_2C_1$-$C_6$alkyl, $NHSO_2R^7$, $PO(OR^7)_2$, $NR^7R^7$, $NR^7COH$, $NR^7COC_1$-$C_6$-alkyl, $NR^7CON(R^7)_2$, $NR^7COW$, W, $SO_2W$;

m is 0–4;

$R^2$ is $C_2$-$C_{10}$alkyl, $C_3$-$C_{10}$alkenyl, $C_3$-$C_{10}$alkynyl, $C_3$-$C_6$cycloalkyl, or $(CH_2)_{0-8}$phenyl unsubstituted or substituted by one to three substituents selected from $C_1$-$C_6$alkyl, nitro, Cl, Br, F, I, hydroxy, $C_1$-$C_6$alkoxy, $NR^7R^7$, $CO_2R^7$, CN, $CONR^7R^7$, W, tetrazol-5-yl, $NR^7COC_1$-$C_6$alkyl, $NR^7COW$, $SC_1$-$C_6$alkyl, $SO_2W$, or $SO_2C_1$-$C_6$alkyl;

X is a single bond, S, $NR^7$, or O;

$R^3$ is hydrogen, Cl, Br, F, I, CHO, hydroxymethyl, $COOR^7$, $CONR^7R^7$, $NO_2$, W, CN, $NR^7R^7$, or phenyl; 7R7

$R^4$ and $R^5$ are independently hydrogen, $C_1$-$C_6$alkyl, thienyl-Y—, furyl-Y—, pyrazolyl-Y—, imidazolyl-Y—, pyrrolyl-Y—, triazolyl-Y—, oxazolyl-Y—, isoxazolyl-Y—, thiazolyl-Y—, pyridyl-Y—, or tetrazolyl-Y—, except that $R^4$ and $R^5$ are not both selected from hydrogen and $C_1-C_6$alkyl and each heterocyclic ring is unsubstituted or substituted by $C_1-C_6$alkyl, $C_1-C_6$alkoxy, Cl, Br F, I, $NR^7R^7$, $CO_2R^7$, $SO_2NHR^7$, $SO_3H$, or $CONR^7R^7$, OH, $NO_2$, W, $SO_2W$, $SC_1-C_6$alkyl, $SO_2C_1-C_6$alkyl, $NR^7COH$, $NR^7COW$, or $NR^7COC_1-C_6$alkyl;

Y is a single bond, O, S, or $C_1-C_6$alkyl which is straight or branched or optionally substituted by phenyl or benzyl, wherein each of the aryl groups is unsubstituted or substituted by halo, $NO_2$, $CF_3$, $C_1-C_6$alkyl, $C_1-C_6$alkoxy, CN, or $CO_2R^7$;

$R^6$ is $-Z-COOR^8$ or $-Z-CONR^7R^7$;

Z is a single bond, vinyl, $-CH_2-O-CH_2-$, methylene optionally substituted by $C_1-C_6$alkyl, one or two benzyl groups, thienylmethyl, or furylmethyl, or $-C(O)NHCHR^9-$, wherein $R^9$ is H, $C_1-C_6$alkyl, phenyl, benzyl, thienylmethyl, or furylmethyl;

W is $C_nF_{2n+1}$, $C_nF_{2n+1}$, wherein n is 1–3;

A is $-(CH_2)_m-$, $-CH=CH-$, $-O(CH_2)_n-$, or $-S(CH_2)_n-$;

each $R^7$ independently is hydrogen, $C_1-C_6$alkyl, or $(CH_2)_m$phenyl, wherein m is 0–4; and $R^8$ is hydrogen, $C_1-C_6$alkyl, or 2-di($C_1-C_6$alkyl)-amino-2-oxoethyl; or a pharmaceutically acceptable salt thereof.

Preferably, one of $R^4$ and $R^5$ is hydrogen or $C_1-C_6$alkyl.

Preferred compounds of this invention are represented by Formula (I) when:

$R^1$ is phenyl or naphthyl with each aryl group being unsubstituted or substituted by one to three substituents selected from chloro, fluoro, trifluoromethyl, nitro, methyl, methoxy, hydroxy, sulfamyl, carboxy, $-(CH_2)_{1-2}$carboxy, $-CH=CH$-carboxy, $OCH_2$-carboxy, carbo$C_1-C_6$alkoxy, carbamoyl, cyano, or tetrazol-5-yl;

m is 0–2;

X is a single bond or S;

$R^2$ is $C_2-C_8$alkyl;

$R^3$ is hydrogen, chloro, fluoro, or trifluoromethyl;

$R^4$ is hydrogen or $C_1-C_6$alkyl;

$R^5$ is thienylmethyl, thienylethyl, furylmethyl, imidazolylmethyl, or pyridylmethyl, each of which is optionally substituted by methyl or methoxy; and $R^6$ is COOH, COO$C_{1-2}$alkyl, or $CONH_2$; or a pharmaceutically acceptable salt thereof.

The E isomers (trans stereochemistry of the $R^6$ group and imidazole group) are generally more active and thus, are preferred over the Z isomers (cis).

As used herein, the terms alkyl, alkenyl, alkoxy and alkynyl mean carbon chains which are branched or unbranched with the length of the chain determined by the descriptor preceding the term.

Particular compounds of the invention include, but are not limited to, the following:

(E)-3-[2-n-butyl-1-{(2-chlorophenyl)methyl}-1H-imidazol-5-yl]-2-(2-thienyl)methyl-2-propenoic acid, (E)-3-[2-n-butyl-1-{(2-chlorophenyl)methyl}-1H-imidazol-5-yl]-2-(2-furyl)methyl-2-propenoic acid, (E)-3-[2-n-butyl-1-{(2-chlorophenyl)methyl}-1H-imidazol-5-yl]-2-(4-pyridyl) methyl-2-propenoic acid, (E)-3-[2-n-butyl-1-{(2-chlorophenyl)methyl}-1H-imidazol-5-yl]-2-(3-thienyl)methyl-2-propenoic acid, (E)-3-[2-n-butyl-1-{(2-chlorophenyl)methyl}-1H-imidazol-5-yl]-2-(5-methyl-2-thienyl)methyl-2-propenoic acid, (E)-3-[2-n-butyl-1-{(2-chlorophenyl)methyl}-1H-imidazol-5-yl]-2-(4-imidazolyl)methyl-2-propenoic acid, (E)-3-[2-n-butyl-1-{(4-carboxyphenyl)methyl}-1H-imidazol-5-yl]-2-(2-thienyl)methyl-2-propenoic acid, (E)-3-[2-n-butyl-1-{(2-nitrophenyl)methyl}-1H-imidazol-5-yl]-2-(2-thienyl)methyl-2-propenoic acid, (E)-3-[2-n-butyl-1-{(2-cyanophenyl)methyl}-1H-imidazol-5-yl]-2-(2-thienyl)methyl-2-propenoic acid, (E)-3-[2-n-butyl-1-{(4-methoxy-3-methylphenyl)methyl}-1H-imidazol-5-yl]-2-(2-thienyl)methyl-2-propenoic acid, (E)-3-[2-n-butyl-1-{(2-chlorophenyl)methyl}-1H-imidazol-5-yl]-2-(5-methoxy-2-thienyl)methyl-2-propenoic acid, (E)-3-[2-n-butyl-1-{(2,3-dichlorophenyl)methyl}-1H-imidazol-5-yl]-2-(2-thienyl)methyl-2-propenoic acid, (E)-3-[2-n-butyl-1-{(4-carboxy-2-chlorophenyl)methyl}-1H-imidazol-5-yl]-2-(2-thienyl)methyl-2-propenoic acid, (E)-3-[2-n-butyl-1-{(4-carboxy-3-chlorophenyl)methyl}-1H-imidazol-5-yl]-2-(2-thienyl)methyl-2-propenoic acid, (E)-3-[2-n-hexyl-1-{(4-carboxyphenyl)methyl}-1H-imidazol-5-yl]-2-(2-thienyl)methyl-2-propenoic acid, (E)-3-[2-n-butyl-1-{(4-carbomethoxyphenyl)methyl}-1H-imidazol-5-yl]-2-(2-thienyl)methyl-2-propenoic acid, (E)-3-[2-n-butyl-1-{(4-carboxynaphth-1-yl)methyl}-1H-imidazol-5-yl]-2-(2-thienyl)methyl-2-propenoic acid, (E)-3-[2-n-butyl-1-{(4-carboxy-2,3-dichlorophenyl) methyl}-1H-imidazol-5-yl]-2-propenoic acid, (E)-3-[2-n-butyl-1-{(3,4-dicarboxyphenyl)methyl}-1H-imidazol-5-yl]-2-(2-thienyl)methyl-2-propenoic acid, (E)-3-[2-n-butyl-1-{(4-carboxyphenyl)methyl}-1H-imidazol-5-yl]-2-(2-thienyl)ethyl-2-propenoic acid, (E)-3-[2-n-butyl-1-{(4-carboxymethylphenyl)methyl}-1H-imidazol-5-yl]-2-(2-thienyl)methyl-2-propenoic acid, (E)-3-[2-n-butyl-1-{(4-carboxy-3-hydroxyphenyl)methyl}1H-imidazol-5 -yl]-2-(2-thienyl)methyl-2propenoic acid, and (E)-3-[2-n-butyl-1-{(2-trifluoromethylphenyl)methyl}-1H-imidazol-5-yl]-2-(2-thienyl)methyl-2-propenoic acid; or a pharmaceutically acceptable salt thereof.

The most preferred compound of this invention is (E)-3-[2-n-butyl-1-{(4-carboxypenyl)methyl}-1H-imidazol-5-yl]-2-(2-thienyl)methyl-2-propenoic acid methanesulfonate.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of producing antihypertensive activity and methods of treating congestive heart failure, glaucoma, and renal failure by administering these compounds are also included in this invention.

The compounds of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The starting materials, 2-$R^2$X-imidazole, are known to the art (J. Org. Chem. 45:4038, 1980) or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran (THF).

The following procedure is useful for the preparation of compounds of Formula (I) particularly where $R^1$ is 2-chlorophenyl or 4-carboxyphenyl, $R^2$ is n-butyl or n-propyl, X is a single bond or S, $R^3$ is hydrogen, chloro, or $CF_3$, $R^4$ is hydrogen, $R^5$ is as described in Formula (I), $R^6$ is $COOR^8$ and $R^8$ is hydrogen, methyl, or ethyl.

The 1-$R^1(CH_2)_m$-group is incorporated onto the 2-$R^2$X-imidazole by known procedures, for example, by reaction with an $R^1$—$CH_2$ halide mesylate or acetate, such as 2-chlorobenzyl bromide, in a suitable solvent, such as dimethylformamide (DMF), in the presence of a suitable acid acceptor, such as sodium alkylate, potassium or sodium carbonate, or a metal hydride, preferably sodium hydride at a reaction temperature of about 25° C. to about 100° C., preferably at about 50° C. The resulting 1-$R^1(CH_2)_m$-2-$R^2$X-imidazole is hydroxymethylated in the 5-position, for example, by reacting with formaldehyde in the presence of sodium acetate in acetic acid to provide the 1-$R^1CH_2$-2-$R^2$X-5-hydroxymethylimidazole intermediates.

Alternatively, the 1-$R^1(CH_2)_m$-2-$R^2$-5-hydroxymethylimidazole intermediates are prepared by reacting an imido ether, $R^2$—C(=NH)—O-alkyl, such as valeramidine methyl ether, with dihydroxyacetone in liquid ammonia under pressure to give 2-$R^2$-5-hydroxymethylimidazole. This intermediate is reacted with acetic anhydride to give 1-acetyl-5-acetoxymethyl-2-$R^2$-imidazole. The diacetate intermediate is N-alkylated, for example, using 2-chlorobenzyl triflate and the resulting 1-$R^1(CH_2)_m$-2-$R^2$-5-acetoxy-methylimidazole is treated with aqueous base, such as 10% sodium hydroxide solution, to give the 1-$R^1(CH_2)_m$-2-$R^2$-5-hydroxymethylimidazole intermediate.

Alternatively, the 2-$R^1$S-imidazole compounds are prepared by the following procedure. Benzylamines, substituted by one to three substituents selected from halo, $C_{1-6}$alkyl, $C_{1-6}$alkoxy, CN, $NO_2$, $CF_3$, $CO_2C_{1-6}$alkyl, $SC_{1-6}$alkyl, or $SO_2C_{1-6}$alkyl, are alkylated with a $C_{1-6}$alkyl chloroacetate, for example methyl chloroacetate, in the presence of a base, such as triethylamine, in a suitable solvent, such as dimethylformamide. The resulting alkylaminoalkyl ester compounds are N-formulated with formic acid in the presence of a suitable solvent, such as xylenes, followed by C-formulation of the carbon alpha to both the amino and the ester groups. Reaction of this intermediate with acidic thiocyanate, preferably potassium thiocyante, in an inert organic solvent, such as a $C_{1-4}$alkyl alcohol, produces 1-$RCH_2$-2-mercapto-5-alkanoate ester imidazole compounds. The free thio group of the ester imidazole is reacted with a halo-$R^{10}$ compound, wherein $R^{10}$ is $C_{2-10}$alkyl, $C_{3-10}$alkenyl, $C_{3-10}$alkynyl, $C_3$-$C_6$cycloalkyl or an optionally substituted $(CH_2)_{0-8}$phenyl, preferably propyl bromide, in the presence of a suitable base, such as sodium carbonate, in an appropriate solvent, such as ethyl acetate. The ester is reduced to the hydroxymethylimidazole intermediate by reduction with a suitable reagent, preferably diisobutyl aluminum hydride, in an appropriate solvent, such as tetrahydrofuran, at a temperature of about −78° C. to about 25° C., preferably at less than −10° C.

The hydroxymethyl group of the hereinbefore prepared intermediate is oxidized to an aldehyde by treatment with a suitable reagent, such as anhydrous chromic acid-silica gel in tetrahydrofuran or, preferably, with activated manganese dioxide, in a suitable solvent, such as benzene or toluene, or preferably methylene chloride, at a temperature of about 25° C. to about 140° C., preferably at about 25° C. The 1-$R^1(CH_2)_m$-2-$R^2$X-imidazol-5-carboxaldehydes are reacted with an appropriate phosphonate, such as those listed in Table I (Examples 2–5). The phosphonates are prepared, for example, from trialkyl phosphonoacetates by alkylation with an appropriate halide, mesylate or acetate in the presence of a suitable base, such as sodium hydride, in a suitable solvent, preferably glyme at a reaction temperature of about 25° C. to about 110° C., preferably at about 55° C., to provide, for example, the phosphonates listed in Table I. The reaction of the imidazol-5-carboxaldehydes with the phosphonates is performed in the presence of a suitable base, such as a metal alkoxide, lithium hydride or preferably sodium hydride, in a suitable solvent, such as ethanol, methanol, ether, dioxane, tetrahydrofuran, or preferably glyme, at a reaction temperature of about 10° C. to about 50° C., preferably at about 25° C., to provide a variable mixture of trans and cis, e.g., (E) and (Z), 1-$R^1(CH_2)_m$-2-$R^2$X-5-CH=C($R^5$)-(COOalkyl)-imidazoles. These isomers are readily separated by chromatography over silica gel in suitable solvent systems, preferably hexane in ethyl acetate mixtures. The esters are hydrolyzed to the acids, 1-$R^1$-$(CH_2)_m$-2-$R^2$X-5-CH=C($R^5$)COOH-imidazoles, using bases, such as potassium hydroxide, lithium hydroxide or sodium hydroxide, in a suitable solvent system, such as, for example, aqueous alcohols or diglyme. The trans and cis structures of the acids are readily determined by NMR by the NOE protocol, as well as by the biological activities since, generally, the trans (E) isomeric acids are the more potent isomers.

Alternatively, the 1-$R^1$ $(CH_2)_m$-2-$R^2$X-imidazol-5-carboxaldehydes are prepared by the following procedure. Starting 2-$R^2$X-imidazol-5-carboxaldehydes are reacted with an N-alkylating protecting reagent, such as chloromethyl pivalate (POM-Cl), in the presence of a base, such as potassium carbonate, in a suitable solvent, such as dimethylformamide, at a temperature of about 20° C. to about 50° C., preferably at about 25° C., to give N-alkylation (e.g., POM-derivation) on the least hindered nitrogen atom of the imidazole nucleus. The 1-$R^1$ $(CH_2)$m-group is incorporated onto the imidazole by N-alkylation of the above prepared aldehyde with a halomethylbenzene compounds, such as methyl 4-bromomethyl-3-chlorobenzoate, at a temperature of about 80° C. to about 125° C., preferably at about 100° C. The protecting group on the 3-nitrogen of the imidazole ring is removed by base hydrolysis, for example using a biphasic mixture of ethyl acetate and aqueous sodium carbonate, to give 1-$R^1CH_2$-2-$R^2$X-imidazole-5-carboxaldehyde compounds. The Formula (I) compounds can be prepared from these 5-carboxaldehyde compounds by the methods described above.

Compounds of Formula (I), wherein $R^6$ is $COOR^8$, $R^1$, $R^2$, $R^3$, $R^4$ and $R^5$ are as described in Formula (I)

and $R^8$ is H, methyl or ethyl, are also prepared by the following procedure.

The 2-$R^2$X-imidazole starting materials are reacted with trimethylsilylethoxymethyl (SEM) chloride to give 1-(trimethylsilyl)ethoxymethyl-2-$R^2$X-imidazole. The reaction is carried out, for example, in the presence of sodium hydride in a solvent such as dimethylformamide. The 5-tributyltin derivatives are prepared by lithiation with, for example, butyllithium in a suitable solvent, preferably diethyl ether, followed by treatment of the lithio imidazole derivative with a tributyltin halide, preferably tri-n-butyltin chloride, at about $-10°$ C. to about 35° C., preferably at about 25° C. The 1-SEM-2-$R^2$X-5-tributyltinimidazole is coupled with an $\alpha,\beta$-unsaturated acid ester having a leaving group on the $\beta$-position, such as a halide or trifluoromethanesulfonyloxy group, for example, BrCR$^4$=C(R$^5$) (COOalkyl), in the presence of a phosphine ligand, such as bis(diphenyl-phosphino)propane, or triphenylphosphine and a palladium (II) compound, or preferably tetrakis(triphenylphosphine)-palladium(O), with or without a base, such as tributylamine, at a temperature of about 50° C. to about 150° C., preferably at about 120° C. Both the (E) and (Z) olefinic isomers are prepared by this procedure, and the isomeric esters are readily separated by chromatography over silica gel. The 1-SEM group from the (E) and (Z) isomers is hydrolyzed with acid, for example, aqueous hydrochloric, in a suitable alcoholic solvent, such as methanol or ethanol, and the 1-unsubstituted imidazole derivatives are converted to the 1-t-butoxycarbonyl (t-BOC) imidazoles with di-t-butyl dicarbonate (Hoppe-Seyler's Z. Physiol. Chem., (1976), 357, 1651). The t-BOC esters are alkylated and hydrolyzed with, for example, 2-chlorobenzyl-O-triflate in the presence of a suitable base, preferably diisopropylethylamine, in a suitable solvent, preferably methylene chloride, to afford the 1-(2-chlorophenyl)-methylimidazole derivatives (esters). The (E) and (Z) isomers are hydrolyzed to the (E) and (Z) acids by the method described above.

Compounds of Formula (I) are also prepared by the following procedure. The 1-$R^1$(CH$_2$)$_m$-2-$R^2$X-imidazole-5-carboxaldehydes, prepared as described above, are reacted with a substituted half-acid, half-ester derivative of a malonate, such as ethyl 2-carboxy-3-(2-thienyl)propionate, in the presence of a base, such as piperidine, in a suitable solvent, such as toluene, at a temperature of about 80° C. to about 110° C., preferably at about 100° C. The resulting 1-$R^1$(CH$_2$)$_m$-2-$R^2$X-5-CH=C(R$^5$) COOalkylimidazoles are hydrolyzed to the corresponding Formula (I) acid compounds by alkaline hydrolysis as described above.

Compounds of Formula (I) in which $R^1$ is 2-chlorophenyl or 4-carboxyphenyl, $R^2$ is n-butyl or n-propyl, X is a single bond or S, $R^3$ is H, Cl or CF$_3$, $R^4$ is methyl, $R^5$ is as described in Formula (I), $R^6$ is COOR$^8$ and other parameters are as described above are prepared as follows. The 1-$R^1$(CH$_2$)$_m$-2-$R^2$X-imidazol-5-carboxaldehydes, prepared as described above, are converted to the corresponding alcohols with an organo-metallic derivative or Grignard reagent, preferably methyl lithium, in a suitable solvent, such as tetrahydrofuran. The alcohol is oxidized, for example, using manganese dioxide to give the ketone. The olefinic esters are prepared from the ketone by reaction with appropriate phosphonates to give the (E) and/or (Z) isomers which are readily separated. The acids are prepared from the esters by alkaline hydrolysis as described above.

Compounds of Formula (I) in which $R^3$ is H, Cl, CH$_2$OH, or CF$_3$ are prepared as follows. The 1-$R^1$-(CH$_2$)$_m$-2-$R^2$X-imidazol-5-carboxaldehydes are treated with the lithium derivative of a substituted ethyl or methyl ester. These lithio derivatives are prepared from the reaction of lithium diisopropylamide in a suitable solvent, preferably tetrahydrofuran, with an acid ester, such as ROOC—CH$_2$—Y-(2-thienyl), to generate the a-lithio derivatives at about $-78°$ C. to about $-10°$ C., preferably at about $-78°$ C., which are then treated with the imidazol-carboxaldehyde. The intermediate $\beta$-hydroxy group of the imidazole ester is converted to a mesylate or an acetate and the mesylate, or preferably the acetate, is heated in a suitable solvent, such as toluene, with one to two equivalents of 1,8-diazobicyclo[5.4.0]undec-7-ene, at about 50° to about 110° C. preferably at about 80° C., to afford ester compounds of Formula (I) such as 3-(imidazol-5-yl)-2-(2-thienyl)methyl-2-propenoic acid esters. The (E) isomer is the predominate olefinic isomer. The acids are prepared from the esters by the method described above.

Compounds of Formula (I), wherein $R^1$ is 2-chlorophenyl or 4-carboxyphenyl, $R^2$ is n-butyl or n-propyl, X is a single bond or S, $R^3$ is H, Cl, CF$_3$, or CH$_2$OH, $R^4$ is H, $R^5$ is heterocyclic or a substituted heterocyclic group as described in Formula (I) and $R^6$ is COOH, may be prepared by heating 1-$R^1$—(CH$_2$)$_m$-2-$R^2$X-imidazol-5-carboxaldehydes at about 50° C. to about 180° C., preferably at about 140° C., with an appropriate substituted heterocyclic acetic acid and with acetic anhydride and potassium carbonate to provide unsaturated acids of Formula (I), such as 3-[2-n-butyl-1-(2-chlorophenyl)methyl-1H-imidazol-5-yl]-2-R$^5$-2-propenoic acid. The trans olefinic acid is the principal product.

Compounds of Formula (I) in which $R^6$ is Z—COOR$^8$ where Z is an optionally substituted methylene group are prepared by reducing the trans or (E) isomers of 3-(imidazol-5-yl)-2-propenoic acid esters (prepared as described above) with an appropriate hydride reagent, preferably diisobutylaluminum hydride, in a suitable solvent, such as tetrahydrofuran, to provide the unsaturated alcohol compounds. These compounds are reacted with ethyl chloroformate, for example, with a base, preferably triethylamine, in a suitable solvent, such as tetrahydrofuran, to give 5-EtOOCOCH$_2$CR$^5$=CR$^4$-imidazoles which are reacted with carbon monoxide in the presence of a phosphine ligand, preferably triphenyl-phosphine with palladium (II) acetate, in a suitable solvent, preferably tetrahydrofuran, at a temperature of about 25° C. to about 100° C., preferably at about 40° C. to give the 5-EtOOCCH$_2$CR$^5$=CR$^4$-imidazoles. The corresponding acids are prepared from these ethyl esters by base hydrolysis as described above.

Compounds of Formula (I) in which Z is —CH$_2$COOR$^8$ having additional substitution on the carbon a to the carboxylate group are prepared by converting 5-EtOOCH$_2$CR$^5$=CH$^4$-imidazoles to the lithium derivative of the ester with a lithium dialkylamide, preferably lithium diisopropylamide, and then treating with an alkylating agent, such as methyl halide, benzyl bromide, or heterocyclic methyl halide, to provide the monoalkylated product compounds or the dialkylated product compounds. The acid compounds are prepared from the esters by base hydrolysis.

Compounds of Formula (I) in which $R^6$ is $Z$—$COOR^8$ where Z is —$CH_2$—O—$CH_2$— are prepared from unsaturated alcohol compounds, which had been obtained by the reduction of the Formula (I) propenoic acid esters. The alcohol is reacted with an appropriate hydride reagent, such as sodium hydride, in a suitable solvent, such as glyme, followed by reaction with an alkylating reagent, such as methyl bromoacetate, to give the 5-MeOOCCH$_2$—O—CH$_2$CR$^5$=CR$^4$-imidazoles. The corresponding acids are prepared from these esters by base hydrolysis as described above.

Compounds of Formula (I) in which $R^6$ is Z—$COOR^8$ where Z is —C(O)NHCHR$^9$— are prepared from the Formula (I) propenoic acid compounds. These acids are reacted with an appropriately substituted amino acid, such as glycine methyl ester hydrochloride or phenylalanine methyl ester hydrochloride, in the presence of an amide-forming reagent, such as N-hydroxysuccinimide and dicyclohexylcarbodiimide, in the presence of a base, for example triethylamine, in a suitable solvent, such as tetrahydrofuran, at a temperature of about 20° C. to about 50° C., preferably at about 35° C. The 5-$C_{1-4}$alkyl-OOCCHR$^9$NH-C(O)—CH$_2$CR$^5$=CR$^4$-imidazoles are converted to their corresponding acids by base hydrolysis as described above.

Compounds of Formula (I) in which the $R^1$ substituent is substituted by hydroxy are formed from Formula (I) compounds in which the $R^1$ group is substituted by $C_1$–$C_4$alkoxy using an ether-cleaving reagent, such as boron tribromide or hydrobromic acid.

Compounds of Formula (I) in which the $R^1$ substituent is substituted by carboxy are formed from Formula (I) compounds in which the $R^1$ group is substituted by $CO_2C_1$–$C_4$alkyl using basic hydrolysis, such as aqueous sodium or potassium hydroxide in methanol or ethanol, or using acidic hydrolysis, such as aqueous hydrochloric acid.

Compounds of Formula (I) in which the $R^1$ substituent is substituted by a tetrazol-5-yl group are prepared from the correponding carboxy compounds. For example, Formula (I) acid compounds are reacted with a halogenating agent, such as thionyl chloride, in a suitable solvent, for example benzene, to give the corresponding acid halide compounds. The acid halides are then converted to primary amide compounds in a reaction with concentrated ammonia. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with aluminum chloride, in a suitable solvent, for example tetrahydrofuran. The Formula (I) compounds in which $R^6$ is —Z—$CO_2H$ are prepared from these Formula (I) tetrazole ester compounds by basic hydrolysis as described above.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) in which $R^8$ is H are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., *Circ. Res.* 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the $IC_{50}$ of compounds of the invention (E isomers) is about 0.1 nM to about 100 mM.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) are calculated by the dose ratio method using the mean effective concentrations. Exemplary of the $K_B$ of compounds of the invention (E isomers) is about 0.1 nM to about 30 mM.

Inhibition of pressor response to angiotensin II in conscious rats

Rats are prepared with indwelling femoral arterial and venous catheters and a stomach tube (Gellai et al., *Kidney Int.* 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 0.1 to 300 mg/kg. The dose of compound needed to produce 50% inhibition of the control response to angiotensin II ($IC_{50}$) is used to estimate the potency of the compounds. The $IC_{50}$ of (E)-3-[2-n-butyl-1-{(2-chlorophenyl)-methyl}-1H-imidazol-5-yl]-2-(2-thienyl)methyl-2-propenoic acid is 3.60 mg/kg i.v. and 44.00 mg/kg orally.

Antihypertensive activity

The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg ($IC_{30}$) is used as an estimate of potency. The $IC_{30}$ of (E)-3-[2-n-butyl-1-{(2-chlorophenyl)methyl}-1H-imidazol-5-yl]-2-(2-thienyl)methyl-2-propenoic acid is 1.80 mg/kg i.v. and 8.0 mg/kg orally.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01–200 mg/kg of active compound, preferably 1–100 mg/kg. The selected dose is administered to a human patient in need of angiotensin II receptor antagonism from 1–6 times daily, orally, rectally, topically, by injection, or continuously by infusion. Oral dosage units for human administration preferably contain from 1 to 500 mg of active compound. Preferably, lower dosages are used for parenteral administration. Oral administration, at higher dosages, however, also can be used when safe and convenient for the patient. Topical formulations contain the active compound in an amount selected from 0.0001 to 0.1 (w/v %), preferably from 0.0001 to 0.01. As a topical dosage unit form, an amount of active compound from between 50 ng to 0.05 mg, preferably 50 ng to 5 mg, is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the method of treating congestive heart failure, glaucoma, and renal failure comprise administering a compound of Formula (I) to a subject in need thereof an effective amount to produce said activity.

Contemplated equivalents of Formula (I) compounds are compounds otherwise corresponding thereto wherein substituents have been added to any of the unsubstituted positions of the Formula (I) compounds provided such compounds have the pharmaceutical utility of Formula (I) compounds.

The following examples illustrate preparation of compounds and pharmaceutical compositions of this invention. The examples are not intended to limit the scope of this invention as defined hereinabove and as claimed below.

EXAMPLE 1

(E)-3-[2-n-Butyl-1-{(2-chlorophenyl)methyl}-1H-imidazol-5-yl]-2-(2-thienyl)methyl-2-propenoic Acid (i)  2-n-butyl-1-(2-chloro-phenyl)methyl-1H-imidazole Imidazole was converted to the 1-diethoxyorthoamide derivative by the method of Curtis and Brown, J. Org. Chem., (1980), 45, 20. Imidazole (12.8 g, 0.19 mol) and 118.4 g (0.8 mol) of triethylorthoformate were reacted in the presence of 1 g of p-toluenesulfonic acid to give 20.6 (61%), bp 65°–70° C. (0.1 mm) of 1-diethoxyorthoamide imidazole. This product (24.0 g, 0.14 mol)

was dissolved in dry tetrahydrofuran (250 mL), cooled to −40° C. and n-butyl lithium (0.14 mol, 56.4 mL of 2.5M in hexane) was added at −40° C. to −35° C. After 15 minutes n-butyl iodide (31.1 g, 0.169 mol) was added at −40° C. and the reaction was stirred overnight at ambient temperature. The reaction was partitioned between ether and 0.3N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of sodium methoxide (from sodium hydride (2.31 g, 0.0934 mol) in methanol (250 mL)). After one hour the solution was evaporated to dryness, and the sodium salt was taken up in dry dimethylformamide (150 mL) and 2-chlorobenzyl bromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-1-(2-chlorophenyl)methyl-1H-imidazole as an oil. Thin layer chromatography on silica gel with 4:1 ethyl acetate/hexane gave an $R_f$ value of 0.59.

(ii) 2-n-butyl-1-(2-chlorophenyl)methyl-5-hydroxymethyl-1H-imidazole

Method 1

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)-methyl-5-hydroxymethyl-1H-imidazole; mp 86°-88° C. (from ethyl acetate). Further elution provided the bis (4,5-hydroxymethyl) derivative; mp 138°-140° C. (from ethyl acetate).

Method 2

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3L). The resulting slurry was refluxed with added acetonitrile (1L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (253 g) was treated with acetic anhydride (400 mL) at −15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl-2-n-butylimidazole.

This diacetate was N-alkylated by the following procedure. To a solution of triflic anhydride (120 mL, 0.71 mol) in methylene chloride (200 mL) at −78° C. under argon was added a solution of diisopropyl ethylamine (128 mL, 0.73 mol) and 2-chlorobenzyl alcohol (104 g, 0.72 mol) in methylene chloride (350 mL) over a period of 20 minutes. After being stirred an additional 20 minutes at −78° C., this solution was then treated with 1-acetyl-4-acetoxymethyl-2-n-butylimidazole (146 g, 0.61 mol) dissolved in methylene chloride (300 mL) over a 20-minute interval. The mixture was then stirred at ambient temperature for 18 hours and the solvents were evaporated. The residual 2-n-butyl-5-acetoxymethyl-1-(2-chlorophenyl)methyl-1H-imidazole was used without purification for the hydrolysis of the acetate group.

A solution of crude 2-n-butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, methylene chloride was added, the organic phase was separated, washed with water, dried and concentrated. The residue was dissolved in ether, cooled, and seeded to give the crude product. Recrystallization from ethyl acetate gave 176 g of 2-n-butyl-1-(2-chlorophenyl)methyl-5-hydroxymethyl-1H-imidazole; mp 86°-88° C. This material was identical in all respects to the product prepared by Method 1.

(iii) 2-n-butyl-1-(2-chlorophenyl)methyl-1H-imidazol-5-carboxaldehyde

A solution of 2-n-butyl-1-(2-chlorophenyl)methyl-5-hydroxymethyl-1H-imidazole (5.4 g, 0.0194 mol) in toluene (25 mL) was added to a suspension of activated manganese dioxide (27 g) in methylene chloride (325 mL). The suspension was stirred at room temperature for 17 hours. The solids were filtered and the filtrate concentrated and flash chromatographed over silica gel with 6:4 hexane/ethyl acetate to afford 4.16 g (78%) of 2-n-butyl-1-(2-chlorophenyl)methyl-1H-imidazol-5-carboxaldehyde, as an oil. NMR and IR were consistent with the structure.

(iv) (E)-3-[2-n-butyl-1-{(2-chloropheny)methyl}-1H-imidazol-5-yl]-2-(2-thienyl)methyl-2-propenoic acid Method A (a) trimethyl 3-(2-thienyl)-2-phosphonopropionate To a solution of 2-thiophenemethanol (2.28 g, 0.02 mol) in carbon tetrachloride (25 mL) was added triphenylphosphine (6.81 g, 0.026 mol), and the solution was refluxed for 3 hours. The cooled reaction mixture was diluted with hexane (60 mL), chilled and filtered. The concentrated filtrate (4.6 g) was flash chromatographed over silica gel with 7:3 hexane/ethyl acetate to provide 2-chloromethylthiophene (1.52 g, 57%) as an oil.

A suspension of sodium hydride (0.271 g, 11.3 mmol) in dry glyme (40 mL) under argon was treated dropwise with trimethyl phosphonoacetate (1.87 g, 10.3 mmol) in glyme (5 mL). The resulting mixture was stirred at room temperature for 1.5 hours. Then 2-chloromethylthiophene (1.5 g, 11.3 mmol) was added, and the mixture was stirred at 65° C. for 18 hours. The reaction was partitioned between water and ethyl acetate, and the organic layer was washed with water and brine, dried with anhydrous magnesium sulfate and concentrated to 1.9 g of an oil. This was chromatographed over silica gel 4:1 ethylacetate/hexane to afford 800 mg (28%) of trimethyl 3-(2-thienyl)-2-phosphonopropionate.

(b) methyl (E)-3-[2-n-butyl-1-{(2-chlorophenyl)methyl}-1H-imidazol-5-yl-2-(2-thienyl)methyl-2-propenoate To a suspension of sodium hydride (69 mg, 2.87 mmol) in glyme (5 mL) was added dropwise a solution of trimethyl 3-(2-thienyl)-2-phosphonopropionate in glyme (3 mL) under an atomsphere of argon. When the gas evolution had subsided, the mixture was heated to 50° C. for 15 minutes. A solution of 2-n-butyl-1-(2-chlorophenyl)methyl-1H-imidazol-5 -carboxaldehyde (0.53 g, 1.92 mmol) in glyme (3 mL) was added, and the mixture was stirred at 60°-65° C. for 5 hours. The cooled reaction was partitioned between water and ethyl acetate, and the organic layer was washed with water, dried, concentrated and flash chromatographed over silica gel to give 336 mg (41%) of methyl (E)-3-[2-n-butyl-1-[(2-chlorophenyl)methyl]-1H-imidazol-5-yl[-2-(2-thienyl)methyl-2-propenoate as an oil whose NMR was entirely consistent with the trans or E form of the olefin.

(c) (E)-3-[2-n-butyl-1-{(2-chlorophenyl)methyl}-1H-imidazol-5-yl]-2-(2-thienyl)methyl-2-propenoic acid A solution of methyl (E)-3-[2-n-butyl-1-[(2-chlorophenyl)methyl]-1H-imidazol-5-yl]-2-(2-thienyl)methyl-2-propenoate (336 mg, 0.783 mmol) in ethanol (10 mL) was treated with 10% sodium hydroxide solution (4 mL), and the solution was stirred for 3 hours at 25° C. The pH was adjusted to 5 and a solid precipitated. The mixture was diluted with water, cooled and filtered to provide 309 mg of solid. A crystallization from ethyl acetate gave 195 mg (60%) of (E)-3-[2-n-butyl-1-[(2-chlorophenyl)methyl]-1H-imidazol-5-yl]-2-(2-thienyl)-methyl-2-propenoic acid; mp 177°-179° C.

Method B (a) methyl 3-[2-n-butyl-1-{(2-chlorophenyl)methyl}-1H-imidazol-5-yl]-3-hydroxy-2-(2-thienyl)methyl-propanoate To a solution of diisopropylamine (1.96 g, 0.0194 mol) in dry tetrahydrofuran (40 mL) held at −78° C. under argon was added n-butyl lithium (7.3 mL, 0.0183 mol of 2.5M in toluene), and the mixture was stirred for 10 minutes. Then, methyl 3-(2-thienyl) propanoate (2.83 g, 0.0166 mol) in tetrahydrofuran (2 mL) was added, and the mixture was stirred for 30 minutes at −78° C. A solution of 2-n-butyl-1 -(2-chlorophenyl)methyl-1H-imidazol-5-carboxaldehyde (3 g, 0.0111 mol) in tetrahydrofuran (4 mL) was added, and the resulting mixture was stirred at −78° C. for 30 minutes. The reaction was partitioned between saturated ammonium chloride solution and ether, the organic extract was washed with brine, dried over anhydrous magnesium sulfate and concentrated to 6.67 g of crude product. This was flash chromatographed over 70 g of silica gel with 4:1 ethyl acetate/hexane to provide 4.03 g (81%) of methyl 3-[2-n-butyl-1-(2-chlorophenyl)methyl-1H-imidazol-5-yl]-3-hydroxy-2-(2-thienyl)methyl-propanoate.

(b) methyl 3-acetoxy-3-[2-n-butyl-1-(2-chlorophenyl)methyl-1H-imidazol-5-yl]-2-(2-thienyl)methylpropanoate A solution of methyl 3-[2-n-butyl-1-(2-chlorophenyl)methyl-1H-imidazol-5-yl]-3-hydroxy-2-(2-thienyl)-methylpropanoate (4.03 g, 9.02 mmol) in methylene chloride (100 mL) was treated with 4-dimethylaminopyridine (0.386 g, 3.16 mmol). Then acetic anhydride (8.5 mL, 9.02 mmol) was added dropwise to the stirred mixture. The mixture was stirred for 18 hours, water (35 mL) was added, the mixture was stirred for 1 hour and then diluted with ether and saturated sodium bicarbonate solution. The ether layer was washed with brine, dried with anhydrous magnesium sulfate and evaporated to give the title 3-acetoxy derivative as an oil (4.37 g, 99%).

(c) methyl (E)-3-[2-n-butyl-1-{(2-chlorophenyl)methyl}-1H-imidazol-5-yl]-2-(2-thienyl)methyl-2-propenoate A mixture of methyl 3-acetoxy-3-[2-n-butyl-1-(2-chlorophenyl) methyl-1H-imidazol-5-yl]-2-(2-thienyl)-methylpropanoate (4.36 g, 8.92 mmol) in dry toluene (80 mL) was treated with 1,8-diazabicyclo[5.4.0 ]undec-7-ene (DBU) (3.2 mL, 21.4 mmol), and the resulting solution was heated at 80° C. under argon for 3 hours. The solvent was evaporated, the residue triturated with ether and activated charcoal was added. After filtration, the filtrate was concentrated to 6.29 g of an oil that was chromatographed over silica gel with 65:35 hexane/ethyl acetate to give 2.89 g (76%) of methyl (E)-3-[2-n-butyl-1-[(2-chlorophenyl)methyl]-1H-imidazol-5-yl]-2-(2-thienyl)-methyl-2-propenoate whose NMR and TLC (50% ethyl acetate in hexane on silica gel) were identical to the product prepared by Method A.

(d) (E)-3-[2-n-butyl-1-{(2-chlorophenyl)methyl}-1H-imidazol-5-yl]-2-(2-thienyl)methyl-2-propenoic acid Basic hydrolysis of this ester (2.88 g, 6.71 mmol) according to Method A (iii) gave 2.59 g (93%) of (E)-3-[2-n-butyl-1-[(2-chlorophenyl)methyl]-1H-imidazol-5-yl]-2-(2-thienyl)methyl-2-propenoic acid; mp 175°-177° C. that was identical to the product from Method A.

EXAMPLES 2–5

In Table I are listed other examples of alkenoic acids prepared from 2-n-butyl-1-(2-chlorophenyl)methyl-1H-imidazol-5-carboxaldehyde by the methods described in Example 1 (Method A). The reagents and products are shown in Table I.

TABLE I

| | Alkenoic Acids | | | | |
|---|---|---|---|---|---|
| | | | | Products (percentage yield) | |
| | | | | (E) H\C=C/CO$_2$R $(a)$IM/ \R$^1$ | (Z) H\C=C/R$^1$ $(a)$IM/ \CO$_2$R |
| Example | Reactant[b] | R | R$^1$ | | |
| 1 | (MeO)$_2$P(O)CH(CH$_2$-2-thienyl)-COOMe[c] | Me | H 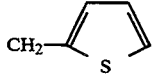 | oil mp 177-179° C. (70) | — |

TABLE I-continued

Alkenoic Acids

| | | | | Products (percentage yield) | |
|---|---|---|---|---|---|
| | | | | (E) H\C=C/CO2R (a)IM/ \R1 | (Z) H\C=C/R1 (a)IM/ \CO2R |
| Example | Reactant[b] | R | R1 | | |
| 2 | (MeO)$_2$P(O)CH(CH$_2$-2-furyl)-COOMe[c] | Me | H, CH$_2$-(2-furyl) | oil (38) mp 180.5–182° C. (73) | oil (21) mp 134.5–136° C. (38) |
| 3 | (MeO)$_2$P(O)CH(CH$_2$-3-furyl)COOMe[c] | Me | H, CH$_2$-(3-furyl) | oil (39) mp 167.5–169° C. (57) | oil (24) — |
| 4 | (MeO)$_2$P(O)CH(CH$_2$-4-(1-tosyl)imidazole)COOMe[c] | Me | H, CH$_2$-(imidazole) | oil mp 230–231° C. (70) | — — |
| 5 | (MeO)$_2$P(O)CH(CH$_2$-3-thienyl)-COOMe[c] | Me | H, CH$_2$-(3-thienyl) | oil (50) mp 192–193.5° C. (74) | oil (38) mp 128.5–130° C. (48) |

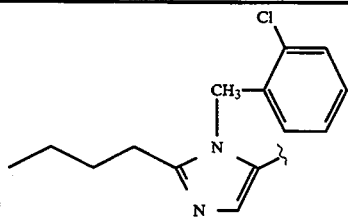

[a]IM =

[b]Prepared as in c;

[c]Reactants for 2-5 prepared as in Method A(i), Example 1 except 2-chloromethylfuran, 3-chloromethylfuran, 4-acetoxymethyl-1-tosylimidazole, and 3-chloromethylthiophene are used in place of 2-chloromethylthiophene.

EXAMPLE 6

(E and Z)-3-[2-n-Butyl-1-{(2-chlorophenyl)methyl)}-1H-imidazol-5-yl]-2-(5-methyl-2-furyl)methyl-2-propenoic Acid

Method A

To a suspension of sodium hydride (0.02 mol) in glyme (30 mL) is added dropwise under argon trimethyl 3-(5-methyl-2-furyl)-2-phosphonopropionate (0.02 mol). After one hour at ambient temperature, 2-n-butyl-1-(2-chlorophenyl) methyl-1H-imidazol-5-carboxaldehyde (0.0137 mol) is added, and the mixture is stirred at 40° C. for one hour. The reaction is quenched with ice water, the product extracted into ether and solvent evaporated to give methyl (E)-3-[2-n-butyl-1-{(2-chlorophenyl)methyl}-1H-imidazol-5-yl]-2-(5-methyl-2-furyl)methyl-2-propenoate. The (E) ester is dissolved in ethanol (4 mL) and 10% sodium hydroxide solution (0.5 mL) is added. The solution is stirred at 25° C. under argon for 17 hours, 10% hydrochloric acid solution is added to pH 3.5 and the solid is filtered, washed with water, and dried at 40° C. in vacuum to give E-3-[2-n-butyl-1-{(2-chlorophenyl)-methyl}-1H-imidazol-5-yl]-2-(5-methyl-2-furyl) methyl-2propenoic acid.

Method B

(i) 2-n-butyl-1-(trimethylsilyl)ethoxymethylimidazole

Hexane-washed 80% sodium hydride (1.45 g, 0.0483 mol) in dimethylformamide (80 mL) under argon was treated with a solution of 2-n-butylimidazole (5.45 g, 0.0439 mol) in dimethylformamide (14 mL) dropwise at 25° C. and the reaction was stirred an additional hour. Then 2-(trimethylsilyl)ethoxymethyl chloride (SEM-Cl) (7.68 g, 0.0461 mol) was added, the mixture was stirred for 18 hours at ambient temperature and then partitioned between ice water and ethyl acetate. The washed, dried, concentrated organic solution was chromatographed over silica gel with 1:1 hexane in ethyl acetate to yield 10.8 g (96%) of 2-n-butyl-1-(trimethylsilyl)ethoxymethyl-imidazole.

(ii) 2-n-butyl-5-tributyltin-1-(trimethylsilyl)ethoxymethylimidazole

A solution of 2-n-butyl-1-SEM imidazole (prepared above) (6.37 g, 0.025 mol) in ethyl ether (125 mL) was treated dropwise with n-butyl lithium (0.0255 mol, 10.2 mL of 2.5M in hexane) under argon at room temperature. After being stirred for an additional 45 minutes, tributyltin chloride (8.83 g, 7.4 mL, 0.026 mol) was added dropwise. The suspension was stirred overnight, saturated ammonium chloride solution was added and the ether layer was separated, washed with brine, dried over sodium sulfate, concentrated and flash chromatographed over silica gel with 3:1 hexane/ethyl acetate to provide 11.3 g (83%) of 2-n-butyl-5-tributyltin-1-(trimethylsilyl)ethoxymethylimidazole.

(iii) ethyl (E and Z)-3-[2-n-butyl-1-{(trimethylsilyl)ethoxymethyl}-1H-imidazol-5-yl]-2-(5-methyl-2-furyl)methyl-2-propenoate To a solution of n-butyl-5-tributyltin-1-(trimethylsilyl)ethoxymethylimidazole (0.0208 mol) in m-xylene (150 mL) is added ethyl 3-bromo-2-(5-methyl-2-furyl)-methyl-2-propenoate (0.0233 mol), followed by tetrakis (triphenylphosphine) palladium (0) (0.416 mmol). The reaction mixture is heated at 120° C. for 18 hours under argon. The cooled mixture is washed with water, 10% ammonium hydroxide solution and brine. The solution is treated with charcoal and sodium sulfate, filtered, concentrated and chromatographed over silica gel with 9:1 hexane in ethyl acetate to give ethyl (Z)-3-[2-n-butyl-1-{(trimethylsilyl)ethoxymethyl}-1H-imidazol-5-yl]-2-(5-methyl-2-furyl)methyl-2-propenoate.

(iv) ethyl (E and Z)-3-[3-n-butyl-1-t-butoxycarbonyl-1H-imidazol-5-yl]-2-(5-methyl-2-furyl)methyl-2-propenoate A solution ethyl (E)-3-[2-n-butyl-1-{(trimethylsilyl)ethoxymethyl}-1H-imidazol-5-yl]-2-(5-methyl-2-furyl)-methyl-2-propenoate (1.24 g, 3.52 mmol) in ethanol (10 mL) is heated at 60° C. for 3.5 hours with 5N hydrochloric acid solution (20 mL). The cooled reaction is basified with 10% sodium hydroxide solution, extracted with ethyl acetate, washed with water, dried and concentrated. The residue is dissolved in methanol (15 mL), triethylamine (1.5 mL, 10.6 mmol), and di-tert-butyldicarbonate (2.3 g, 10.5 mmol) are added and the mixture is stirred for 18 hours at ambient temperature. The mixture is concentrated in vacuo and chromatographed over silica gel with 4:1 hexane/ethyl acetate to give ethyl (Z)-3-[2-n-butyl-1-t-butoxycarbonyl-1H-imidazol-5-yl]-2-(5-methyl-2-furyl)methyl-2-propenoate as an oil. The (E)-isomer was prepared by the same procedure described for the (Z)-isomer.

(v) ethyl (E and Z)-3-[2-n-butyl-1-{(2-chlorophenyl)methyl}-1H-imidazol-5-yl]-2-(5-methyl-2-furyl)-methyl-2-propenoate To a stirred solution of trifluoromethanesulfonic anhydride (387 mg, 1.37 mmol) in methylene chloride (1 mL) held at −75° C. under argon is added a solution of 2-chlorobenzyl alcohol (196 mg, 1.37 mmol) and diisopropylethylamine (177 mg, 1.37 mmol) in methylene chloride (4 mL). After stirring for 20 minutes at −75° C., a solution of ethyl (Z)-3-[2-n-butyl-1-t-butoxycarbonyl-1H-imidazol-5-yl]-2-(5-methyl-2-furyl)methyl-2-propenoate in methylene chloride (2 mL) is added dropwise over 10 minutes and the mixture was stirred overnight at 25° C. A solution of 5% sodium bicarbonate solution is added with stirring and the layers are separated, washed and dried. The reaction mixture is evaporated to dryness, the residue triturated with 1:1 hexane/ethyl acetate, the solid filtered off and the filtrate is concentrated and chromatographed over silica gel with 7:3 hexane/ethyl acetate to provide the title compound. The title (E)-isomer is prepared by the same procedure described for the (Z) isomer.

(vi) (Z)-3-[2-n-butyl-1-{(2-chlorophenyl)methyl}-1H-imidazol-5-yl]-2-(5-methyl-2-furyl)methyl-2-propenoic acid The title compounds are prepared by basic hydrolysis of the corresponding ethyl esters according to the procedure described in Example 6, Method A.

EXAMPLE 7

(E)-3-[2-n-Butyl-1-{(2-chlorophenyl)methyl)}-1H-imidazol-5-yl]-2-(3-thienyl)methyl-2-butenoic Acid (i) 2-n-butyl-1-(2-chlorophenyl)methyl-5-(α-hydroxy) ethyl-1H-imidazole A solution of 2-n-butyl-1-(2-chlorophenyl)methyl-1H- imidazol-carboxaldehyde (Example 1 (iii)) (1.1 g, 3.97 mmol) was dissolved in dry tetrahydrofuran (15 mL), cooled to −78° C. under argon and a solution of methyl lithium (3.64 ml of 1.2M in diethyl ether, 4.57 mmol) was added dropwise. The mixture was stirred for 1.5 hours, quenched with ammonium chloride solution, warmed to ambient temperature and extracted with ethyl acetate. The washed, dried, concentrated product was flashed chromatographed over silica gel with ethyl acetate to provide 1.07 g (92%) of 2-n-butyl-1-(2-chlorophenyl)methyl-5-(a-hydroxy) ethyl-1H-imidazole.

(ii) [2-n-butyl-1-{(2-chlorophenyl)methyl}-1H-imidazol-5-yl]methyl ketone

A mixture of 2-n-butyl-1-(2-chlorophenyl)methyl-5-(α-hydroxy)ethyl-1H-imidazole (1.07 g, 3.65 mmol), activated manganese dioxide (6 g) and toluene (75 mL) was heated at 90° to 100° C. under a slight vacuum with a Dean Stark water separator for 17 hours. The inorganics were filtered, the concentrated filtrate was applied to a flash silica gel column and the product was eluted with 3:7 hexane/ethyl acetate to give 0.628 g (59%) of [2-n-butyl-1-{(2-chlorophenyl)methyl}-1H-imidazol-5-yl]methyl ketone.

(iii) methyl (E)-3-[2-n-butyl-1-{(2-chlorophenyl)methyl}-1H-imidazol-5-yl]-2-(3-thienyl)methyl-2-butenoate To absolute ethanol (3 mL) is added freshly cut sodium (55 mg). Then trimethyl 3-(3-thienyl)-2-phosphonopropionate (2.16 mmol) and [2-n-butyl-1-{(2-chlorophenyl)methyl}-1H-imidazole-5-yl]methyl ketone (0.628 g, 2.16 mmol) are added and the mixture is stirred at 70° C. for 17 hours. The reaction is concentrated, partitioned between ethyl acetate and water, and the organic layer was washed with water, dried, concentrated and chromatographed to afford the title compound.

(iv) (E) -3-[2-n-butyl-1-{(2-chlorophenyl) methyl}-1H-imidazol-5-yl]-2-(3-thienyl)methyl-2-butenoic acid The title compound is prepared according to Example 1 (Method A, iii) by using methyl (E)-3-[2-n-butyl-1-{(2-chlorophenyl)methyl}-1H-imidazol-5-yl]-2-(3-thienyl)methyl-2-butenoate in place of methyl (E)-3-[2-n-butyl-1-{(2-chlorophenyl) methyl}-1H-imidazol-5-yl]-2-(2-thienyl)methyl-2-propenoate.

EXAMPLE 8

(E)-3-[2-n-Butyl-1-{(2-chloro-6-fluoro-phenyl)methyl}-1H-imidazol-5-yl]-2-(2-thienyl)-methyl-2-propenoic Acid (i) 2-n-butyl-1-(2-chloro-6-fluorophenyl)methyl-1H-imidazole A solution of 2-n-butylimidazole (3.75 g, 0.03 mol) in dry dimethylformamide (4 mL) was added to sodium hydride (0.95 g) in dimethylformamide (18 mL). After the gas evolution subsided, the mixture was stirred one hour under argon and 2-chloro-6-fluorobenzylchloride (5.5. g, 0.031 mol) in dimethylformamide (7 mL) was added to produce an exotherm. The mixture was stirred for 17 hours at ambient temperature, diluted with ice water and extracted with ethyl acetate. The washed, dried, concentrated organic layer provided 7.63 (94%) of the title compound whose NMR was consistent with the structure. This material was used without further purification.

(ii) 2-n-butyl-1-(2-chloro-6-fluorophenyl)-methyl-1H-imidazol-5-carboxaldehyde

The procedures of Example 1(ii–iii) were used. From 7.63 g of crude 2-n-butyl-1-(2-chloro-6-fluorophenyl)-methyl-1H-imidazole and proportional amounts of other reagents was obtained 2.8 g of 2-n-butyl-1-(2-chloro-6-fluorophenyl)methyl-5-hydroxymethyl-1H-imidazole after chromatography over silica gel with 3% of methanol in methylene chloride; mp 106°–108° C. (from ethyl acetate). This material was oxidized with manganese dioxide and worked up as described above to give 0.88 g (63%) of 2-n-butyl-2-(2-chloro-6-fluorophenyl)methyl-1H-imidazol-5-carboxaldehyde; mp 88°–90° C. (from ethyl acetate).

(iii) (E)-3-[2-n-butyl-1-{(2-chloro-6-fluorophenyl)methyl}-1H-imidazol-5-yl]-2-(2-thienyl)methyl-2-propenoic acid The procedure of Example 1, Method A is used. 2-n-Butyl-1-(2-chloro-6-fluorophenyl)-methyl-1H-imidazole-5-carboxaldehyde, trimethyl 3-(2-thienyl)-2-phosphonopropionate, sodium hydride and glyme are held at 60° C. for 1 hour to give, after chromatography over silica gel with 50% of hexane in ethyl acetate, methyl (E)-[2-n-butyl-1-{(2-chloro-6-fluorophenyl)methyl}-1H-imidazol-5-yl]-2-(2-thienyl)methyl-2-propenoate and corresponding cis or (Z)-isomer. The (E)-isomer is hydrolyzed to afford (E)-3-[2-n-butyl-1-{(2-chloro-6-fluorophenyl)methyl}-1H-imidazol-5-yl]-2-(2-thienyl)-methyl-2-propenoic acid.

EXAMPLE 9

(E)-3-[2-n-Butyl-1-{(2-chlorophenyl)methyl}-1H-imidazol-5-yl]-2-(2-thienyl)-2-propenoic Acid A mixture of 2-n-butyl-1-(2-chlorophenyl)methyl-1H-imidazol-5-carboxaldehyde (2 mmol), 2-thienylacetic acid (2.3 mmol), potassium carbonate (0.91 mmol), and acetic anhydride (1 mL) is heated gradually to 140° C. and held at this temperature for 6 hours. The cooled reaction is diluted with water and the solid is separated, triturated several times with ether, and the solid is crystallized to give the title compound.

EXAMPLE 10

(E)-3-[2-n-Butyl-1-{(2-chlorophenyl)methyl}-1H-imidazol-5-yl]-2-(2-furyl)-2-propenoic Acid This compound is prepared according to Example 9, using 2-furylacetic acid in place of 2-thienylacetic acid.

EXAMPLE 11

(E)-3-[2-n-Butyl-1-{(2-chlorophenyl)methyl}-1H-imidazol-5-yl]-2-(2-thienyl)methyl-2-heptenoic Acid (i) Ethyl 3-trifluoromethane-sulfonyloxy-2-heptenoate Ethyl 3-ketoheptanoate (2.07 g, 12 mmol) was dissolved in dimethylformamide (60 mL) under argon and sodium hydride (357 mg, 14.4 mmol) was added. After 30 minutes at room temperature the solid N-phenyltrifluoro-methanesulfonamide (*Tetra. Letters*, (1983), 24, 979) (4.97 g, 13.8 mmol) was added. The reaction was stirred for 2 hours, diluted with ether/water and the usual workup gave after chromatography with 5:95 ether/hexane 3.45 g (94%) of ethyl 3-trifluoromethanesulfonyloxy-2-heptenoate.

(ii) ethyl (E) -3-[2-n-butyl-1-{(trimethylsilyl)ethoxymethyl}-1H-imidazol-5-yl]-2-(2-thienyl)methyl-2-heptenoate A solution of 2-n-butyl-5-tributyltin-1-(trimethylsilyl)ethoxymethyl imidazole (Example 6, Method B (ii)) (3.63 mmol) and ethyl 3-trifluoromethanesulfonyloxy-2-(2-thienyl)methyl-2-heptenoate (3.62 mmol) in tetrahydrofuran (5 mL) is added to a mixture of lithium chloride (11.1 mmol) and tetrakis(triphenylphosphine)palladium (0) (0.076 mmol) in tetrahydrofuran (10 mL). The reaction is heated to reflux under argon for 5 hours, cooled, diluted with ether and the ether layer is washed with water, 10% ammonium hydroxide solution and brine. The extract is dried with sodium sulfate and concentrated. The product is chromatographed over silica gel with a gradient of hexane in ethyl acetate to give the title compound.

(iii) ethyl (E)-3-[2-n-butyl-1-{(2-chlorophenyl)methyl}-1H-imidazol-5-yl]-2-(2-thienyl)methyl-2-heptenoate The procedure of Example 6, Method B (iv, v) is followed using ethyl (E)-3-[2-n-butyl-1-{(trimethylsilyl)ethoxymethyl}-1H-imidazol-5-yl]-2-(2-thienyl)methyl-2heptenoate in in place of ethyl (E)-3-[2-n-butyl-1-{(trimethylsilyl) ethoxymethyl}-1H-imidazol-5-yl]-2-(5-methyl-2-furyl)methyl-2-heptanoate to give the title compound.

(iv) (E)-3-[2-n-butyl-1-{(2-chlorophenyl)methyl}-1H-imidazol-5-yl]-2-(2-thienyl)methyl-2-heptenoic acid The ethyl ester, prepared above, is dissolved in ethanol and 10% sodium hydroxide solution is added. An additional 1 ml of base is added incrementally over several hours and the mixture is stirred overnight at room temperature. The cooled reaction was acidified to pH 5 with dilute hydrochloric acid solution, extracted with methylene chloride and the resulting residue is triturated with ether/hexane to provide the title compound.

EXAMPLE 12

(E)-3-[2-n-Butyl-1-{(2-chlorophenyl)methyl}-1H-imidazol-5-yl]-4-(3-thienyl)-2-butenoic Acid (i) Ethyl 4-(3-thienyl)-3-trifluoromethanesulfonyloxy-2-butenoate This compound was prepared according to Example 11(i) using ethyl 4-(3-thienyl)-3-ketobutanoate in place of ethyl 3-ketoheptanoate.

(ii) ethyl (E)-3-[2-n-butyl-1-{(trimethylsilyl)-ethoxymethyl}-1H-imidazol-5-yl]-4-(3-thienyl)-2-butenoate To a solution of 2-n-butyl-1-SEM-imidazole (Example 6, Method B(i)) (5.32 mmol) in ethyl ether (16 mL) is added n-butyl lithium in hexane (6.5 mmol) at a slow rate. After an additional hour of stirring at 25° C., a solution of zinc chloride in ether (6.5 mL of 1.0M) is added followed by tetrahydrofuran (15 mL). After an additional 75 minutes of stirring, the zinc chloride imidazole adduct solution is transferred under argon to a solution of ethyl 4-(3-thienyl)-3-trifluoromethane-sulfonyloxybutenoate (6.41 mmol) and tetrakis(triphenylphosphine)palladium(0) (317 mg) in tetrahydrofuran (30 mL). The reaction mixture is stirred at 25° C. for 20 hours and worked up as in Example 12 (ii) to provide ethyl (E)-3-[2-n-butyl-1-{(trimethylsilyl)ethoxymethyl}-1H-imidazol-5-yl]-4-(3-thienyl )-2-butenoate.

(iii) ethyl (E)-3-[2-n-butyl-1-{(2-chlorophenyl)methyl}-1H-imidazol-5-yl]-4-(3-thienyl )-2-butenoate The title compound is prepared according to the procedure of Example 6, Method B(iv, v) using ethyl (E)-3-[2-n-butyl-1-{(trimethylsilyl)ethoxymethyl}-1H-imidazol-5-yl]-4-(3-thienyl)-2-butenoate in place of ethyl (E)-3-[2-n-butyl-1-{(trimethylsilyl)ethoxymethyl}-1H-imidazol-5-yl]-2-(5-methyl-2-furyl)methyl-2-propenoate. The title compound is an oil.

(iv) (E)-3-[2-n-butyl-1-{(2-chlorophenyl)methyl}-1H-imidazol-5-yl]-4-(3-thienyl)-2-butenoic acid The above ethyl ester (520 mg) is dissolved in ethanol (5 mL) and 5N hydrochloric acid solution (40 mL), and the solution is slowly heated at 100° C. with evaporation of the alcohol. After being heated at 100° C. for 6 hours, the reaction is cooled and the white precipitate is collected, air-dried, and then triturated with ether/methanol to afford (E)-3-[2-n-butyl-1-{(2-chlorophenyl)-methyl}-1H-imidazol-5-yl]-4-(3-thienyl)-2-butenoic acid hydrochloride.

EXAMPLE 13

(E)-4-[2-n-Butyl-1-{(2-chlorophenyl)-methyl}-1H-imidazol-5-yl]-3-(5-methyl-2-furyl)methyl-3-butenoic Acid (i) (E)-3-[2-n-butyl-1-{(2-chlorophenyl)methyl}-1H-imidazol-5-yl]-2-(5-methyl-2-furyl)methyl-2-propenol A solution of methyl (E)-3-[2-n-butyl-1-{(2-chlorophenyl)methyl}-1H-imidazol-5-yl]-2-(5-methyl-2-furyl)methyl-2-propenoate (Example 6, Method A) (1.5 mmol) in dry tetrahydrofuran (10 mL) held at −78° C. under argon is treated dropwise with a solution of diisobutyl aluminum hydride in toluene (3.30 mmol, 2.2 mL of 1.5M). The mixture is allowed to warm to ambient temperature and stirred an additional 17 hours. Excess reducing agent is quenched with methanol and water, dilute acetic acid and methylene chloride are added, and the organic layer is washed with sodium bicarbonate solution, dried and concentrated to give the title compound.

(ii) ethyl (E)-3-[2-n-butyl-1-{(2-chlorophenyl)methyl}-1H-imidazol-5-yl]-2-(5-methyl-2-furyl)methyl-2-propenyl carbonate To a solution of (E)-3-[2-n-butyl-1-{(2-chlorophenyl)methyl }-1H-imidazol-5-yl]-2-(5-methyl-2-furyl)methyl-2-propenol (6.86 mmol) in methylene chloride (20 mL) and triethylamine (12.4 mmol) cooled to 0° C. under argon is added dropwise ethyl chloroformate (1.34 g, 1.18 ml, 12 mmol). The reaction is then stirred at ambient temperature overnight. Ethyl acetate is added, the precipitate filtered and the concentrated filtrate is flash chromatographed over silica gel with 3:7 hexane/ethyl acetate to provide the title compound.

(iii) ethyl (E)-4-[2-n-butyl-1-{(2-chlorophenyl)methyl)-1H-imidazole-5-yl]-3-(5-methyl-2-furyl)methyl-3-butenoate A solution of ethyl (E)-3-[2-n-butyl-1-{(2-chlorophenyl)methyl}-1H-imidazol-5-yl]-2-(5-methyl-2-furyl)methyl-2-propenyl carbonate (3.77 mmol) in tetrahydrofuran (12 mL) under an atmosphere of carbon monoxide is treated with triphenylphosphine (0.188 mmol) and palladium diacetate and the mixture is heated at 40° C. for 2½ hours. The concentrated reaction mixture is applied to a flash column of silica gel and eluted with 1:1 hexane/ethyl acetate to afford the title compound.

(iv) (E)-4-[2-n-butyl-1-{(2-chlorophenyl)methyl}-1H-imidazol-5-yl]/-3-(5-methyl-2-furyl)methyl-3-butenoic acid The compound is prepared according to the procedure of Example 1, Method A(iii) using the above prepared ethyl ester in place of ethyl (E)-3-[2-n-butyl-1-{(2-chlorophenyl)methyl}-1H-imidazol-5-yl]-2-(2-thienyl)methyl-2-propenoate.

EXAMPLE 14

(E)-4-[2-n-Butyl-1-{(2-chlorophenyl)methyl}-1H-imidazol-5-yl]-2-methyl- and -2,2-dimethyl-3-(2-thienyl)methyl-3-butenoic Acid (i) ethyl (E)-4-[2-n-butyl-1-{(2-chlorophenyl)methyl}-1H-imidazol-5-yl]-2-methyl-3-(2-thienyl)-methyl-3-butenoate Lithium diisopropylamide (0.85 mmol, 1M in tetrahydrofuran) is cooled to −78° under argon and a solution of ethyl (E)-4-[2-n-butyl-1-{(2-chlorophenyl)methyl}-1H-imidazol-5-yl]-3-(2-thienyl)methyl}-3-butenoate (0.709 mmol), prepared as in Example 13 using methyl (E) 3-[2-n-butyl-1-[(2-chlorophenyl)methyl]-1H-imidazol-5-yl]-2-(2-thienyl) methyl-2-propenoate (Example 1), in tetrahydrofuran (5 mL) is added. After 10 minutes methyl iodide (0.71 mmol) is added. The mixture is then stirred at room temperature overnight, diluted with 10% ammonium chloride and extracted with ethyl acetate. The dried, concentrated product is chromatographed over silica gel with 6:4 hexane/ethyl acetate to give the title compound.

(ii) (E)-4-[2-n-butyl-1-{(2-chlorophenyl)methyl}-1H-imidazol-5-yl]-2-methyl-3-(2-thienyl)methyl-3-butenoic acid A solution of the above prepared ethyl ester in ethanol is heated to reflux with 10% sodium hydroxide solution for 2 hours. The ethanol is evaporated, water is added and the aqueous layer is extracted with ether. The water layer is acidified to pH 1 with dilute hydrochloric acid solution, extracted with ethyl acetate, dried and concentrated to a solid. Trituration with ether provides the hydrochloride salt of the title compound.

(iii) (E)-4-[2-n-butyl-1-{(2-chlorophenyl)methyl}-1H-imidazol-5-yl]-2,2-dimethyl-3-(2-thienyl)methyl-3-butenoic acid This compound is prepared according to the procedure of Example 14 (i,ii) using two equivalents of methyl iodide.

EXAMPLE 15

(E)-4-[2-n-Butyl-1-{(2-chlorophenyl)methyl}-1H-imidazol-5-yl]-2-(2-thienyl)methyl-3-(2-thienyl)methyl-3-butenoic Acid This compound is prepared according to the procedure of Example 14(i, ii) using less than one equivalent of 2-chloromethylthiophene in place of methyl iodide.

EXAMPLE 16

(E)-4-[2-n-Butyl-1-{(2-chlorophenyl)methyl}-1H-imidazol-5-yl]-2-benzyl-3-(2-thienyl)methyl-3-butenoic Acid This compound is prepared according to Example 14(i,ii) but using less than one equivalent of benzyl bromide at higher solvent dilution.

EXAMPLE 17

(E,E)-5-[2-n-Butyl-1-{(2-chlorophenyl)methyl}-1H-imidazol-5-yl]-4-(2-thienyl)methyl-2,4-pentadienoic Acid (i) (E)-3-[2-n-butyl-1-{(2-chlorophenyl)methyl}-1H-imidazol-5-yl]-2-(2-thienyl)methyl-2-propenol To a solution of methyl (E)-3-[2-n-butyl-1-{(2-chlorophenyl)methyl}-1H-imidazol-5-yl]-2-(2-thienyl)methyl-2-propenoate, prepared in Example 1, ((2.60 g. 6.06 mmol) in 35 mL of tetrahydrofuran at −78° C. under argon was added a solution of diisobutylaluminum hydride (1.5M, 8.9 mL, 13.3 mmol). After the addition was complete, the reaction mixture was allowed to warm to room temperature, with stirring being continued for one hour. The reaction was worked up by the slow addition of methanol, followed by the addition of glacial acetic acid, then four drops of 10% aqueous hydrochloric acid solution. Water (10 mL) was added and the reaction mixture was stirred at room temperature overnight. The product was extracted with ethyl acetate (3×75 mL) after 40 mL of water had been added to the mixture. The combined extracts were dried with anhydrous magnesium sulfate and the solvents were removed in vacuo. The residue was triturated with diethyl ether. The resulting solid was filtered to give 1.72 g (71%) of product; mp 114°–115° C.

(ii) (E)-3-[2-n-butyl-1-{(2-chlorophenyl)methyl-1H-imidazol-5-yl]-2-(2-thienyl)-methyl-2-propionaldehyde To a suspension of 8.0 g of manganese dioxide in 80 mL of benzene was added (E)-3-[2-n-butyl-1-{(2-chlorophenyl)methyl}-1H-imidazol-5-yl]-2-(2-thienyl)-methyl-2-propenol (1.61 g, 4.02 mmol). The reaction was stirred vigorously for 0.5 hours. The solids were filtered and washed with ethyl acetate. The filtrate was concentrated to near-dryness and then the residue was triturated with hexane. The resulting solid was filtered to give 0.669 g of product; mp 163.5°–164.6° C.

The filter cake was heated with ethyl acetate for 10 minutes and the solids were filtered. The filtrate was cooled in ice/water and the resulting solid was filtered to give 0.712 g of additional product; mp 163.5°–164.5° C.

(iii) ethyl (E,E)5-[2-n-butyl-1-{(2-chlorophenyl)methyl)-1H-imidazol-5-yl]-4-(2-thienyl)-methyl-2,4-pentadienoate To a suspension of (E)-3-[2-n-butyl-1-{(2-chlorophenyl)methyl-1H-imidazol-5-yl]-2-(2-thienyl)methyl-2-propionaldehyde in 8 mL of toluene was added (carbethoxymethyl)triphenylphosphorane. The reaction was heated overnight at 40° C. After cooling to room temperature, the solids were filtered to give 0.181 mg of crude product. Chromatography on silica gel eluting with hexane/ethyl acetate (6:4) gave 0.2345 g (50%) of the title compound as an oil.

(iv) (E,E)-5-[2-n-butyl-1-{(2-chlorophenyl)methyl}-1H-imidazol-5-yl]-4-(2-thienyl)methyl-2,4-pentadienoic acid The title compound was prepared according to the procedure of Example 1 (iv), Method A(c) using the above prepared ethyl ester; hydrochloric acid salt, mp 191°–192.5° C.

Alternately, the sodium salt of the acid is isolated directly from the reaction mixture, prior to neutralization. The crude basic reaction solution is applied to a reverse-phase flash column equilibrated with water. The inorganics are washed from the column with water (3 void volumes) and then the product is eluted with a 50:50 mixture of acetonitrile in water. The acetonitrile is removed in vacuo and then the desired sodium salt is obtained after lyophilization.

EXAMPLE 18

(E)-3-[2-n-Butyl-1-{(2-chlorophenyl)methyl}-1H-imidazol-5-yl]-2-(2-thienyl)methyl-2-propenoic acid, 2-(N,N-Diethylamino)-2-oxoethyl Ester A solution of (E)-3-[2-n-Butyl-1-{(2-chlorophenyl)methyl}-1H-imidazol-5-yl]-2-(2-thienyl)methyl-2-propenoic acid (Example 1) (5 mmol) in dry dimethylformamide (10 mL) was treated with 2-chloro-N,N-diethyl-acetamide (5.51 mmol) followed by powdered potassium carbonate. This mixture was heated at 70° C. for 7 hours, diluted with water and extracted with ethyl acetate. The water-washed, dried, concentrated product solidifies and after trituration with ether/hexane affords the title ester; mp 139°–140° C.

EXAMPLE 19

(E)-3-[2-n-Butyl-1-{(2-chlorophenyl)methyl-4-hydroxymethyl}-1H-imidazol-5-yl]-2-(2-thienyl)methyl-2-propenoic Acid (i) 2-n-butyl-1-(2-chlorophenyl)methyl-4-(t-butyldimethylsilyloxy)-methyl-1H-imidazol-5-carboxaldehyde A solution of 2-n-butyl-1-(2-chlorophenyl)methyl-4,5-bis (hydroxy)methyl-1H-imidazole (Example 1 (ii)) (310 mg, 1 mmol) in methylene chloride (5 mL) was treated with 4-dimethylaminopyridine (5.2 mg), triethylamine (1.5 mmol) and t-butyl dimethylsilyl chloride (192 mg, 1.24 mmol). The mixture was stirred at 25° C. for 20 hours, diluted with water and the organic layer was washed well with water, dried, concentrated and chromatographed over silica gel with an ethyl acetate/methanol gradient to afford 127 mg (24%) of the bis (4,5-t-butyldimethylsilyl) ether and 252 mg (59%) of 2-n-butyl-1-(2-chlorophenyl)methyl-4-t-butyldimethysilyloxymethyl-5-hydroxymethyl-1H-imidazole.

This monoether (252 mg) was oxidized to the 5-carboxaldehyde using manganese dioxide as described in Example 1 (iii) to provide 170 mg of 2-n-butyl-1-(2-chlorophenyl)-methyl-4-(t-butyldimethylsilyloxy)methyl-1H-imidazol-5-carboxaldehyde as an oil.

(ii) ethyl (E)-3-[2-n-butyl-1-{(2-chlorophenyl)methyl]-4-(t-butyldimethyl-silyloxy)methyl}-1H-imidazol-5-yl]-2-(2-thienyl)methyl-2-propenoate In tetrahydrofuran (80 mL) is added n-butyl lithium (15.5 mmol in hexane) and at −78° C. under argon is then added diisopropylamine (2.4 mL, 17.1 mmol). Methyl 3-(2thienyl)propanoate (15.3 mmol) is added neat over 5–6 minutes, and the mixture was stirred an additional 30 minutes at −78° C. A solution of 2-n-butyl-1-(2-chlorophenylmethyl-4-(t-butyldimethyl-silyloxy)methyl-1H-imidazol- 5-carboxaldehyde (10.2 mmol) in tetrahydrofuran (10 mL) is added via cannula, and the reaction mixture is stirred for 15 minutes. The reaction is partitioned between saturated ammonium chloride and ether, and the ether layer is washed with water, dried and concentrated to give crude product. This is chromatographed over silica gel with 20–50% of ethyl acetate in hexane to afford a mixture of isomeric β-hydroxyester products. A solution of this mixture (8.54 mmol) in methylene chloride (100 mL) is treated with 4-dimethylaminopyridine (3 mmol) followed by acetic anhydride (84 mmol), and the solution is stirred at room temperature for 5 hours. The reaction is poured into water, stirred for 20 minutes and the product is extracted into ether. The ether extracts are washed with dilute hydrochloric acid solution, water, sodium bicarbonate solution and brine. The dried, concentrated mixture of β-acetoxyester products is used directly in the elimination reaction. To a solution of the β-acetoxyester product (4.5 mmol) in toluene (60 mL) is added of 1,8-diazabicyclo[5.4.0]undec-7-ene (DBU) (10.9 mmol), and the mixture is heated at 90° C. for 24 hours. The reaction is concentrated to 10 mL, diluted with ether and flash filtered through a 14×3 cm plug of silica gel with ether rinses to afford the crude olefinic product. Chromatography over silica gel with an ethyl acetate in hexane gradient gives homogeneous ethyl (E)-3-[2-n-butyl-1-{(2-chlorophenyl)methyl]-4-t-butyldimethylsilyloxymethyl}-1H-imidazol-5-yl]-2-(2-thienyl)methyl-2-propenoate. The elimination of the acetate with DBU produces predominantly the trans (E)isomer.

(iii) (E)-3-[2-n-butyl-1-{(2-chlorophenyl)methyl-4-hydroxymethyl}-1H-imidazol-5-yl]-2-(2-thienyl)-methyl-2-propenoic acid A solution of ethyl (E)-3-[2-n-butyl-1-{(2-chlorophenyl)-4-t-butyldimethylsilyloxymethyl}-1H-imidazol-5-yl]-2-(2-thienyl)methyl-2-propenoate (0.287 mmol) in absolute ethanol (3 mL) is treated portionwise at 6 hour intervals with 10% sodium hydroxide solution (3×1 mL). After being stirred overnight at 25° C., the reaction is heated to 50° C. for 4 hours, then concentrated in vacuo. The residual product is taken up in water, acidified to pH 5–6 and extracted with methylene chloride. The isolated, dried, concentrated product is triturated with methanol/ether to provide the title compound.

EXAMPLE 20

(E)-3-[2-n-Butyl-1-{(2-chlorophenyl)methyl}-1H-imidazol-5-yl]-2-(4-pyridyl)methyl-2-propenoic Acid (i) methyl 3-[2-n-butyl-1-(2-chlorophenyl)methyl-1H-imidazol-5-yl]-3-hydroxy-2-(4-pyridyl)methylpropanoate To a solution of diisopropylamine (3.58 mL, 25.6 mmol) in dry tetrahydrofuran (50 mL) held at −78° C. under argon was added n-butyl lithium (10.2 mL, 25.6 mmol of 2.5M in toluene), and the mixture was stirred for 10 minutes. Then, methyl 3-(4-pyridyl)propanoate (4.22 g, 25.6 mmol) (prepared by reaction of 4-pyridine carboxaldehyde with trimethyl phosphonoacetate in the presence of sodium hydride in ethylene glycol dimethyl ether, followed by catalytic hydrogenation of the double bond with 10% palladium on carbon at 3 atmosphere of hydrogen in an ethyl acetate solution (98%) to provide the saturated ester) was added in tetrahydrofuran (40 mL) and this mixture was stirred for 30 minutes at −78° C. A solution of 2-n-butyl-1-(2-chlorophenyl)-methyl-1H-imidazol-5-carboxaldehyde (5.9 g, 21.3 mmol) in tetrahydrofuran (10 mL) was added and stirring was continued for 30 minutes at −78° C. The reaction was partitioned between saturated ammonium chloride solution and ether, the organic extract was washed with brine, dried over magnesium sulfate, concentrated and flash chromatographed over silica gel with 5% methanol in ethyl acetate to provide 3.32 g (30%) of methyl 3-[2-n-butyl-1-(2-chlorophenyl)-methyl-1H-imidazol-5-yl]-3-hydroxy-2-(4-pyridyl)methylpropanoate. TLC on silica gel with 5% methanol in ethyl acetate showed a homogenous product with an $R_f$ of 0.79.

(ii) methyl 3-acetoxy-3-[2-n-butyl-1-(2-chlorophenyl)methyl-1H-imidazol-5-yl]-2-(4-pyridyl)-propanoate A solution of methyl 3-[2-n-butyl-1-(2-chlorophenyl)-methyl-1H-imidazol-5-yl]-3-hydroxy-2-(4-pyridyl)-methylpropanoate (3.32 g, 7.5 mmol)methylene chloride (50 mL), 4-dimethylaminopyridine (150 mg, 1.3 mmol) and acetic anhydride (7.1 mL, 75 mmol) was stirred at ambient temperature for 18 hours. Water (5 mL) was added, the mixture was stirred for 2 hours and then diluted with methylene chloride and 5% sodium bicarbonate solution. The organic phase was washed with 5% sodium bicarbonate solution and brine, dried and concentrated to give 4 g of the crude title compound. TLC on silica gel with 5% methanol ethyl acetate showed essentially one spot material with an $R_f$ of 0.86. No starting material was detected. This material was not purified further.

(iii) methyl (E)-3-[2-n-butyl-1-{(2-chlorophenyl)methyl)}-1H-imidazol-5-yl]-2-(4-pyridyl)methyl-2-propenoate A mixture of methyl 3-acetoxy-3-[2-n-butyl-1-(2-chlorophenyl)methyl-1H-imidazol-5-yl]-2-(4-pyridyl) propenoate (7.5 mmol), toluene (50 mL) and 1,8-diazabicyclo[5,4,0]-undec-7-ene (DBU) (3.4 mL, 22.5 mmol) was heated at 90° C. for 18 hours under argon. The cooled mixture was diluted with ether, and washed with brine, dried and concentrated to 3.1 g (97%) of the title compound. NMR showed that the trans or E isomer was the primary product.

(iv) (E)-3-[2-n-butyl-1-{(2-chlorophenyl)methyl}-1H-imidazol-5-yl]-2-(4-pyridyl)-methyl-2-propenoic acid A solution of methyl (E)-3-[2-n-butyl-1-{(2-chlorophenyl)methyl}-1H-imidazol-5-yl]-2-(4-pyridyl) methyl-2-propenoate (3.1 g, 7.3 mmol) in ethanol (16 mL) was treated with 10% sodium hydroxide solution and the mixture was stirred for 18 hours at 25° C. The solution was concentrated in vacuum, water was added, the pH was adjusted to 6.5 and the resulting solid was filtered, washed with water and crystallized from methanol/ether to afford 0.48 g of (E)-3-[2-n-butyl-1-{(2-chlorophenyl)methyl}-1H-imidazol-5-yl]-2-(4-pyridyl)-methyl-2-propenoic acid; mp 178°–182° C. (d).

EXAMPLES 21–26

In Table II are listed other examples of alkenoic acids prepared by the methods described in Example 20 (i–iv). The starting materials and products are shown in Table II.

TABLE II

[Structure: 1-(2-chlorobenzyl)-2-n-butyl-imidazole with CH=C(R⁴)COOH at 5-position and R⁴ at 4-position]

| Example | Starting Materials | R³ | Product (R⁵)[a] | mp |
|---|---|---|---|---|
| 21 | [1-(2-chlorobenzyl)-2-n-butyl-5-CHO-imidazole] (II) + thiophene-CH₂CH₂CH₂CO₂Me | H | –CH₂CH₂–(2-thienyl) | 184–185° C. |
| 22 | (II) + 2-pyridyl-CH₂CH₂COOMe | H | –CH₂–(2-pyridyl) | 156–160° C. (d) |
| 23 | (II) + 3-pyridyl-CH₂CH₂COOMe | H | –CH₂–(3-pyridyl) | 161–164° C. |
| 24 | (II) + 5-methyl-2-thienyl-CH₂CH₂COOMe | H | –CH₂–(5-methyl-2-thienyl) | 169–170° C. |
| 25 | (II) + 3-methyl-2-thienyl-CH₂CH₂COOMe | H | –CH₂–(3-methyl-2-thienyl) | 173.5–175° C.[b] |
| 26 | [1-(2-chlorobenzyl)-2-n-butyl-4-chloro-5-CHO-imidazole] + 2-thienyl-CH₂CH₂COOMe | Cl | –CH₂–(2-thienyl) | 175–176° C.[b] |

[a] Product prepared by the 4 step synthetic route described in Example 20. The penultimate olefinic ester is purified, if necessary, by chromatography over silica gel with ethyl acetate/hexanes or methanol/ethyl acetate mixtures.
[b] Hydrochloride salt.

EXAMPLE 27

By the procedure of Example 20 (i–iv) using in place of methyl 3-(4-pyridyl)propanoate, the following:
methyl 3-(4-thiazolyl) propanoate,
methyl 3-(1,2,3,4-tetrazol-5-yl)propanoate, and
methyl 3-(1-tosylpyrazol-3-yl) propanoate;
the products are:
3-[2-n-butyl-1-{(2-chlorophenyl)methyl}-1H-imidazol-5-yl]-2-(4-thiazolyl)methyl-2-propenoic acid,
3-[2-n-butyl-1-{(2-chlorophenyl)methyl}-1H-imidazol-5-yl]-2-(1,2,3,4-tetrazol-5-yl)methyl-2-propenoic acid, and
3-[2-n-butyl-1-{(2-chlorophenyl)methyl}-1H-imidazol-5-yl]-2-(3-pyrazolyl)methyl-2-propenoic acid.

EXAMPLE 28

(E)-3-[2-n-Butyl-1-{(2-chlorophenyl)methyl}-4-fluoro-1H-imidazol-5-yl]-2-(2-thienyl)methyl-2-propenoic Acid Anhydrous hydrochloric acid (20.5 g, 0.562 mol) bubbled into a stirred solution of valeronitrile (31.8 g, 40.0 mL, 0.383 mol) in methanol (13.47 g, 17 mL, 0.421 mol) which was cooled by a ice/acetone bath. The reaction was capped tightly and then stored at 10° C. overnight. To this solid mixture at 10° C. under argon was added 100 mL of t-butyl methyl ether. Once a free-flowing crystalline mixture had formed, the solid was collected and washed with 400 mL of t-butyl methyl ether. The solid was immediately placed in a vacuum desicator over phosphoric anhydride and sodium hydroxide to give 55.50 g (96%) of valeramidine methyl ether hydrochloride; mp 103°-105° C.

The procedure of W. Lwosski, Synthesis, 263 (1971) was followed. To a mixture of valeramidine methyl ether hydrochloride (37.91 g, 0.25 mol) and 50% aqueous cyanamide (13.53 g, 25 mL, 0.322 mol) cooled in an ice bath was added portionwise anhydrous disodium phosphate (12.01 g, 0.0846 mol). After the addition was complete, the ice bath was removed and an oil and solid began to come out of solution. After stirring for an additional 30 minutes, the oil was decanted from the solid. The solid was partitioned between water and diethyl ether and the oil was also dissolved in diethyl ether. The combined organic extracts were washed with saturated sodium chloride solution and then dried with anhydrous sodium sulfate. The solvent was removed in vacuo to give 33.06 g (94%) of valercyanamidine methyl ether.

To a solution of the amidine methyl ether prepared above (33.06 g, 0.236 mol) in 225 mL of absolute ethanol was added in one portion 2-chlorobenzylamine (33.39 g, 0.236 mol). The reaction was stirred at room temerpature for 2 hours and then the solvent was removed in vacuo to give 55.4 g (94%) of a solid, whose NMR indicated the absence of the methyl ether functionality.

The secondary amine was alkylated using the following procedure. A mixture of the product prepared above (35.0 g, 0.14 mol) and potassium carbonate (67.72 g, 0.49 mol) in 200 mL of dimethylformamide was stirred under argon at 60° C. for 15 minutes. To this mixture was added over 10 minutes ethyl bromoacetate (24.56 g, 0.143 mol). After the addition was complete, the reaction temperature was raised to 75°-80° C. After 30 minutes, the reaction mixture was filtered. The filtrate was concentrated in vacuo. The residue was partitioned between ethyl acetate and water. The organic extract was washed with water (5×) and saturated sodium chloride solution. The organic extract was dried with anhydrous sodium sulfate and then the solvent was removed in vacuo. The crude product was chromatographed on silica gel eluting with ethyl acetate in hexane to give 37.15 g (79%) of an oil.

2-n-Butyl-1-{(2-chlorophenyl)methyl}-4-amino-5-carboethoxyimidazole was prepared by the following procedure. Sodium metal (2.54 g, 0.110 g-atom) was dissolved in absolute ethanol under argon. To this solution was added a solution of the above-prepared product (37.07 g, 0.110 mol) in 175 mL of absolute ethanol over a 15 minute period. After the addition was complete the reaction mixture was stirred for one hour at room temperature. The resulting solid was collected, washed with water, and air-dried to give 25 g of product; mp 120°-121° C.

The 4-amino product was fluorinated using the procedure of K. L. Kirk and L. J. Cohen, JACS, 95 (14), 4619 (1973). Fluoroboric acid (48%, 150 mL) was added to 2-n-butyl-1-{(2-chlorophenyl)methyl}-4-amino-5-carboethoxyimidazole (10.75 g, 0.032 mol) in a quartz flask. The resulting solid mass was sonicated and stirred vigorously to form a suspension. This suspension was cooled to 0° C. and then sodium nitrite (2.80 g, 0.0406 mol) in 5 mL of water was added slowly. The ice bath was removed and then the reaction mixture was irradiated for 20 hours with a 450-watt mercury vapor lamp placed in a quartz immersion well, cooled by circulating water. The reaction mixture was cooled to −20° C. and the pH was adjusted to 6.4 with 50% aqueous sodium hydroxide. The product was extracted into ethyl acetate (3×) and the combined extracts were washed with water and saturated sodium chloride solution. The organic extract was dried with anhydrous sodium sulfate and concentrated to give 8.43 g of a crude product, which was chromatographed on silica gel eluting with chloroform to give 4.31 g of 2-n-butyl-1-{(2-chlorophenyl)methyl}-4-fluoro-5-carboethoxyimidazole.

This carboethoxy compound was converted to the corresponding 5-formyl derivative following the procedure of Example 17 (i and ii).

2-n-Butyl-1-{(2-chlorphenyl)methyl}-4-fluoro-5-formylimidazole was converted to E-3-[2-n-butyl-1-{(2-chlorophenyl)methyl}-4-fluoro-1H-imidazol-5-yl]-2-(2-thienyl)methyl-2-propenoic acid following the procedure of Example 20 (i-iv) replacing methyl 3-(4-pyridyl)propanoate with methyl 3-(2-thienyl)-propanoate; mp 126°-127° C.

EXAMPLE 29

(E)-3-[2-n-Butyl-1-{(2-chlorophenyl)methyl}-4-bromo-1H-imidazol-5-yl]-2-(2-thienyl)methyl-2-propenoic Acid By the procedure of Example 28 using the corresponding 4-bromo starting material (prepared by the method described in U.S. Pat. No. 4,340,598), the title compound is prepared.

EXAMPLE 30

(E)-3-[2-n-Butyl-1-{(2-chlorophenyl)methyl}-4-trifluoromethyl-1H-imidazol-5-yl]-2-(2-thienyl)methyl-2-propenoic Acid Using 2-n-butyl-1-(2-chlorophenyl)methyl-4-trifluoroethyl-1H-imidazol-5-carboxaldehyde (prepared by treating the corresponding 4-bromo compound with trifluoromethyl iodide and copper) in the procedure of Example 20 gives the title compound.

EXAMPLE 31

By the procedure of Example 1, using in place of 2-chlorobenzyl bromide, the following:
2-methylbenzyl bromide,
4-methoxybenzyl bromide, and
4-phenylbenzyl bromide;
and using the phosphonopropionate of Example 1, $(MeO)_2P(O)CH(CH_2-2-thienyl)COOMe$, the following products are obtained:
(E)-3-[2-n-butyl-1-{(2-methylphenyl)methyl}-1H-imidazol-5-yl]-2-(2-thienyl)methyl-2-propenoic acid, (E)-3-[2-n-butyl-1-{(4-methoxyphenyl)methyl}-1H-imidazol-5-yl]-2- (2-thienyl)methyl-2-propenoic acid, and (E)-3-[2-n-butyl-1-{(4-phenylphenyl)methyl}-1H-imidazol-5-yl]-2-(2-thienyl)methyl-2-propenoic acid.

EXAMPLE 32

The following methyl ester of a propenoate are prepared as in Example 31:
  methyl (E)-3-[2-n-butyl-1-[(4-methoxyphenyl)-methyl]-1H-imidazol-5-yl]-2-(2-thienyl)methyl-2-propenoate.

This is treated with boron tribromide in methylene chloride at room temperature for six hours and then the reaction mixture is condensed and treated with a mixture of ethyl acetate and water. The washed ethyl acetate layer gives on evaporation:
(E)-3-[2-n-butyl-1-[(4-hydroxyphenyl)methyl]-1H-imidazol-5-yl]-2-(2-thienyl)methyl-2-propenoic acid.

EXAMPLE 33

(E)-3-[2-(1-Butenyl)-1-{(2-chlorophenyl)methyl}-1H-imidazol-5-yl]-2-(2-thienyl)methyl-2-propenoic Acid A mixture of 2-n-butyl-1-(2-chlorophenyl)methyl-1H-imidazol-5-carboxaldehyde and N-bromosuccinimide in carbon tetrachloride was irradiated to give the 2-(1-bromobutyl)imidazole which was dehydrobrominated by treating 1,8-diazabicyclo[4.5.0]undec-1-ene in tetrahydrofuran to give 2-(1-butenyl)-1-(2-chlorophenyl)methyl-1H-imidazol-5-carboxaldehyde.

The above prepared intermediate and the 3-(2thienyl)propenoate of Example 1 in the procedure of Example 1 was used to give the title compound; mp 224°–226° C.

EXAMPLE 34

(E)-3-[2-Phenyl-1-{(2-chlorophenyl)methyl}-1H, imidazol-5-yl]-2-(2-thienyl)methyl-2-propenoic Acid By the procedure of Example 1(ii) Method 2, using benzamidine methyl ether in place of valeramidine methyl ether, 2-phenyl-5-hydroxymethylimidazole is prepared and converted to 2-phenyl-1-(2-chlorophenyl)methyl-5-hydroxymethyl-1H-imidazole. The 5-hydroxymethyl group is oxidized using manganese dioxide by the procedure of Example 1 (iii). The resulting 2-phenyl-1-(2-chlorophenyl)methyl-1H-imidazol-5-carboxaldehyde is used in the procedure of Example 21 with methyl 3-(2-thienyl)propanoate to give the title compound.

EXAMPLE 35

By the procedure of Example 34 using the following amidine methyl ethers:
  $C_{10}H_{21}C=NH(OCH_3)$ and
  $C_2H_5C=NH(OCH_3)$;
the following products are obtained:
(E)-3-[2-decyl-1-{(2-chlorophenyl)methyl}-1H-imidazol-5-yl]-2-(2-thienyl)methyl-2-propenoic acid and
(E)-3-[2-ethyl-1-{(2-chlorophenyl)methyl}-1H-imidazol-5-yl]-2-(2-thienyl)methyl-2-propenoic acid.

EXAMPLE 36

(E)-3-[2-n-Butyl-1-{(2-chlorophenyl)methyl}-4-formyl-1H-imidazol-5-yl]-2-(2-thienyl)methyl-2-propenoic Acid The title compound is prepared by dilute hydrochloric acid hydrolysis of the 4-t-butyldimethylsilyloxy group of ethyl 3-[2-n-butyl-1-[(2-chlorophenyl)methyl]-4-(t-butyldimethyl-silyloxy)methyl]-1H-imidazol-5-yl]-2-(2-thienyl)methyl-2-propenoate, prepared as in Example 20 (ii), followed by manganese dioxide oxidation of the 4-hydroxymethyl group to the carboxaldehyde.

EXAMPLE 37

3-[1-(2-Adamantyl)ethyl)-2-n-butyl-1H-imidazol-5-yl]-2-(2-thienyl)methyl-2-propenoic Acid A mixture of 2-(1-adamantyl)ethanol (10.7 g and diisopropylethylamine (11 ml) in methylene chloride (70 ml) was added to triflic anhydride (16.75 g) in methylene chloride (70 ml) at −78° C. under argon. After stirring the mixture at −78° C. for 45 minutes, 1-acetyl-2-n-butyl-5 -(acetoxymethyl)imidazole in methylene chloride (50 ml) was added and the mixture was allowed to stand at room temperature for 4 days, then concentrated and heated on a steam bath with 10% sodium hydroxide (250 ml), diluted with 300 ml of water, extracted with methylene chloride, dried, filtered and concentrated to give an oil. Chromatography (silica gel) in methanol-chloroform gives 5-acetoxymethyl-1-[2-(1-adamantyl)ethyl]-2-n-butylimidazole.

The above prepared compound (5.4 g) was stirred at room temperature with potassium hydroxide (5.2 g) in ethanol (200 ml) for one hour. The mixture was concentrated, poured into water, stirred and filtered to give 1-[2-(1-adamantyl)ethyl]-2-n-butyl-5-hydroxymethyl-imidazole. The hydroxymethyl group was oxidized by refluxing the imidazole compound (51.1 g) with manganese dioxide (20.3 g) in toluene (200 ml) to give 1-[2-(1-adamantyl)ethyl]-2-n-butyl-imidazol-5-carboxaldehyde.

Diisopropylamine (0.563 g) was covered with 5 ml of tetrahydrofuran and 2 ml of 2.5M n-butyl lithium in hexane was added at −78° C. The mixture was stirred for 15 minutes, then methyl 3-(2-thienyl) propenoate (0.89 g) in 3 ml of tetrahydrofuran was added. After 20 minutes, 1.04 g of 1-[2-(1-adamantyl)ethyl]-2-n-butyl-imidazol-5-carbox-aldehyde in 3 ml of tetrahydrofuran was added and the mixture was stirred for 30 minutes at −78° C. The mixture was poured into 40 ml of saturated ammonium chloride in water, extracted with ether, dried over magnesium sulfate, filtered, concentrated and chromatographed on silica gel eluting with 70% ethyl acetate and 30% hexane to give methyl 3-[1-(2-(1-adamantyl)ethyl]-2-n-butyl-1H-imidazol-5-yl]-3-hydroxy-2-(2-thienylmethyl)propanoate. To 1.27 g of this compound in methylene chloride (25 ml) was added 4-dimethylaminopyridine (1.25 g), then acetic anhydride (2.75 g) was added dropwise. The mixture was stirred for one hour, then poured into water and worked up to give 3-acetoxy-3-[1-(2-(1-adamantyl)ethyl)-2-n-butyl-1H-imidazol-5yl]-2-(2-thienylmethyl) propanoate.

The above prepared compound (1.2 g) was heated with 1,8-diazabicyclo[5,4,0]undec-7-ene (1 ml) in toluene (20 ml) at 80° C. with stirring for one hour. The mixture was concentrated, then stirred with ether. The ether layer was decanted and dried, filtered, concentrated and chromatographed to give methyl 3-[1-(2-(1- adamantyl)ethyl)-2-n-butyl-1H-imidazol-5-yl]-2-(2-thienylmethyl)-2-propenoate.

This ester (0.63 g) was hydrolyzed in ethanol (10 ml) using potassium hydroxide (0.18 g) to give the title compound; 218°–220° C.

EXAMPLE 38

(E)-3-[2-n-Butyl-1-[(2-chlorophenyl)methyl]-4-carboxy-1H-imidazol-5-yl]-2-(2-thienyl)methyl-2-propenoic Acid (E)-3-[2-n-Butyl-1-[(2-chlorophenyl)methyl]-4-hydroxymethyl-1H-imidazol-5-yl]-2-(2-thienyl)methyl-2-propenoic acid, prepared as in Example 19, is esterified with 4-methoxy-benzyl alcohol to give the p-methoxybenzyl propenoate. The 4-hydroxymethyl group in acetone is oxidized using an acidic aqueous solution containing chromic acid (Jones' reagent) and the ester is hydrolyzed using 10% sodium hydroxide to give the title compound.

EXAMPLE 39

(E)-3-[2-n-Butyl-1-[(2-chlorophenyl)methyl]-4-carbamoyl-1H-imidazol-5-yl]-2-(2-thienyl)methyl-2-propenoic Acid 4-Methoxybenzyl (E)-3-[2-n-butyl-1-[(2-chlorophenyl)methyl]-4-carboxy-1H-imidazol-5-yl]-2-(2-thienyl)methyl-2-propenoate, prepared as in Example 38, is treated with oxalyl chloride in methylene chloride at 0° C. to give the acid halide which is treated with ammonium hydroxide and the ester is hydrolyzed to give the title compound.

EXAMPLE 40

(E)-3-[2-n-Butyl-1-[(2-chlorophenyl)methyl]-4-dimethylcarbamoyl-1H-imidazol-5-yl]-2-(2-thienyl)methyl-2-propenoic Acid Treating the 4-chloroformyl imidazole, prepared as in EXAMPLE 39, with dimethylamine instead of ammonium hydroxide gives the title compound.

EXAMPLE 41

(E)-3-[2-n-Butyl-1-{(4-carboxyphenyl)methyl}-1H-imidazol-5-yl]-2-(2-thienyl)methyl-2-propenoic Acid (i) By the procedure of Example 1 [(ii) Method 2, (iii) and (iv) Method B] using 4-carbomethoxybenzyl alcohol in place of 2-chlorobenzyl alcohol, the title compound was prepared; mp 250°–253° C.

(ii) Preparation of Monomethanesulfonate

The title compound, 3600 g, was added to 2-propanol (54 L) in a 20-gallon, glass-lined reactor. The stirred suspension was cooled to approximately 8° C. Methanesulfonic acid (2448 g) was added rapidly to the vigorously stirred suspension. The starting material dissolved quickly to give a clear solution within two minutes. A slight exotherm to approximately 11° C. was observed. A fine, white solid began to precipitate from the solution within an additional three minutes. The suspension was stirred at a temperature of 3° C. for 5.5 hours and the solid was collected by centrifugation. After washing with 10 L of 2-propanol, the product was dried under vacuum at 45° C. to a constant weight of 4.21 kg (94% yield, uncorrected for assay).

The crude product (4.20 kg) was charged as a solid to 12.6 L of stirred, glacial acetic acid in a 10-gallon, glass-lined reactor. The slurry was heated to 80° C., giving a homogeneous solution. The solution was filtered warm through an in-line filter, and the reactor and filter lines were washed with 4.2 L of additional acetic acid. The combined acetic acid solutions were stirred with slow cooling to 25° C. in a separate 10-gallon, glass-lined reactor. Precipitation of a solid began to occur at about 45° C. After 2.5 hours the suspension was diluted with 42 L of ethyl acetate, added in two equal portions with a one hour interval between additions. The suspension was stirred for an additional 18 hours to allow complete precipitation. The solid product was collected by centrifugation and washed with 10 L of ethyl acetate. After drying to a constant weight under vacuum at 40° C., a recovery of 3.80 kg of product; mp 251°–252° C. (90.4%, uncorrected for assay) was obtained.

EXAMPLE 42

(E)-3-[2-n-Butyl-1-{(4-carboxy-2-chlorophenyl)methyl}-1H-imidazol-5-yl]-2-(2-thienyl)methyl-2-propenoic Acid A suspension of 2-butylimidazol-5-aldehyde (16,92 g, 0.111 mol, prepared by manganese dioxide oxidation of the alcohol, prepared in Example 1,Method 2), chloromethyl pivalate (21.77 g, 0.145 mol), and potassium carbonate (20.07 g, 0.145 mol) in 200 ml of dimethylformamide was stirred at ambient temperature under argon for four days. The solids were removed by filtration and washed with ether. The combined filtrates were partitioned between diethyl ether and water. The ether phase was washed successively with water and brine, dried over magnesium sulfate and concentrated under vaccum to give 23.6 g of 2-n-butyl-1-pivalyloxymethylimidazole-5-aldehyde.

A mixture of ethyl 4-bromomethyl-3-chlorobenzoate (5.28 g, 0.020 mol, U.S. Pat. No. 4,837,333) and 2-n-butyl-1-pivaloyloxymethyl-imidazole-5-aldehyde (4.45 g, 0.0167 mol) was heated at 100° C. under argon for 18 hours. Repeated trituration with ether gave 6.38 g of a crystalline salt. A suspension of this salt in 100 ml of ethyl acetate was stirred for 0.5 hours with 100 ml of 5% aqueous sodium carbonate. The layers were separated, the aqueous layer washed with ethyl acetate, and the combined organic layers washed with water, dried over magnesium sulfate and concentrated to give an oil. Chromatography of this oil over silica eluting gel with ethyl acetate/hexane (1:1) gave 1.02 g of 2-n-butyl-1-[(4-carboethoxy-2-chlorophenyl)methyl]imidazole-5-aldehyde.

Ethyl 2-carboxy-3-(2-thienyl)propionate (14 g, 0.061 mol) was prepared by stirring a solution of diethyl 2-thienylmalonate (16.8 g, 0.0655 mol) and potassium hydroxide (4.41 g, 0.0786 mol) in 200 ml of ethanol under argon at room temperature for 12 days and then purifying by removing the solvent under vacuum, dissolving the reside in water, washing the aqueous layer with aqueous hydrochloric acid and with diethyl ether.

A solution of this half-acid, half-ester (1.05 g, 4.62 mmol) in 5 ml of toluene was added to a refluxing solution of 2-n-butyl-1-[(4-carboethoxy-2-chlorophenyl)methyl]-imidazole-5-aldehyde (1.03 g, 3.08 mmol) and piperidine (0.26 g, 3.08 mmol) in 60 ml of toluene. Twice, at 1 hour intervals, an additional 1 g of the half-acid, half-ester was added, and the solution was then refluxed for 17 hours. Evaporation of the toluene and chromatography of the residue over silica gel using 2:3 ethyl acetate-hexane for elution gave 0.39 g of the diester of the title product. This was hydrolyzed in 2:1 ethanol-water with 5 equivalents of potassium hydroxide for 18 hours and worked up in the usual manner to give 0.260 g of final product; mp 234°-236° C. The NMR of this product was in accord with its structure.

EXAMPLE 43

(E)-3-[2-n-Butyl-1-{(4-sulfonamidophenyl)methyl}-1H-imidazol-5-yl]-2-(2-thienyl)methyl-2-propenoic Acid The procedure of Example 42 is followed using 4-bromomethylbenzenesulfonamide (Braselton, et al., *Anal. Chem.*, 48, 1386 (1976)) in place of methyl 4-bromomethyl-3-chlorobenzoate to give the title compound.

EXAMPLE 44

(E)-3-[2-n-Butyl-1-{(4-carboxy-2-nitrophenyl)methyl}-1H-imidazol-5-yl]-2-(2-thienyl)methyl-2-propenoic Acid The procedure of Example 42 was followed using methyl 4-bromomethyl-3-nitrobenzoate (prepared from 4-methyl-3-nitrobenzoic acid by esterification with gaseous hydrochloric acid-methanol followed by methyl bromination with N-bromosuccinimide) to give the title compound; mp 163° C.

EXAMPLE 45

(E)-3-[2-n-Butyl-1-{(4-carboxy-3-chlorophenyl)methyl}-1H-imidazol-5-yl]-2-(2-thienyl)methyl-2-propenoic Acid The procedure of Example 42 was followed using ethyl 4-bromomethyl-2-chlorobenzoate (U.S. Pat. No. 4,837,333) in place of ethyl 4-bromomethyl-3-chlorobenzoate to give the title compound; 245°-246° C.

EXAMPLE 46

(E)-3-[1-{(2-Chlorophenyl)methyl}-2-propylthio-1H-imidazol-5-yl]-2-(2-thienyl)methyl-2-propenoic Acid (i) 5-carboxymethyl-1-(2-chlorophenyl)methyl-2-thio-1H-imidazole A solution of 2-chlorobenzylamine (14.2 g, 0.1 mol) and triethylamine (13.9 ml, 0.1 mol), in dimethylformamide (100 ml) was treated with methyl chloroacetate (10.9 g, 0.1 mol), and the mixture was heated at 50° C. for 3.5 hours. The cooled reaction mixture was diluted with ether, the solids filtered and the concentrated filtrate was flash chromatographed over silica gel with 6:5 hexane in ethyl acetate to provide 15.3 g (71%) of homogeneous methyl 2-[N-(2-chlorophenyl)methyl]aminoacetate. This product (15.2 g, 0.071 mol) in mixed xylenes (100 ml) was treated with 98% formic acid (2.74 ml), 0.0711 mol) and the mixture was refluxed from 2.5 hours with a Dean-Stark water separator. Evaporation gave 17.1 g (99%) of methyl 2-[N-(2-chlorophenyl)methyl-N-formyl) aminoacetate. This formylated product (17.0 g, 0.071 mol) was dissolved in methyl formate (13.3 ml, 0.216 mol) and added dropwise to a sodium methoxide mixture prepared by adding sodium metal (1.79 g, 0.0778 g-atom) to tetrahydrofuran (325 ml) followed by slow addition of methanol (3.15 ml, 0.0778 mol). The combined mixture was stirred at room temperature for 18 hours, then evaporated to dryness. This crude product was dissolved in 50% aqueous methanol (200 ml), treated with charcoal, filtered and the solution was cooled in ice. Concentrated hydrochloric acid followed by a solution of potassium thiocyanate (8.6 g, 0.0885 mol) in water (20 ml). The mixture was heated in an oil bath held at 90° C. for 2.5 hours, then cooled to 10° C. The precipitated solid was filtered, washed with cold ehtanol-water and dried at 60° C. to provide 14.7 g (74%) of 5-carboxymethyl-1-(2-chlorophenyl)methyl-2-thio-1H-imidazole; mp 72°-74° C.

(ii) 1-(2-chlorophenyl)methyl-5-carboxymethyl-2-propylthio-1H-imidazole

A mixture of 5-carboxymethyl-1-(2-chlorophenyl)methyl-2-thio-1H-imidazole (2 g, 7.08 mmol, ethyl acetate (20 ml), 5% sodium carbonate solution (40 ml) and propyl bromide (4 ml, 44 mmol) was heated at 60° C. for 18 hours. The organic layer was separated, dried over magnesium sulfate and concentrated to 2.23 g of crude product. Trituration with ether provided 1.63 g (71%) of 5-carboxymethyl-1-(2-chlorophenyl)methyl-2-propylthio-1H-imidazole; mp 68°-71° C. (from hexane).

(iii) E-3-[1-(2-chlorophenyl)methyl-2-propylthio-1H-imidazol-5-yl]-2-(2-thienyl)methyl-2-propenoic acid A solution of 5-carboxymethyl-1-(2-chlorophenyl)methyl-2-propylthio-1H-imidazole (3.74 g, 11.5 mmol) in dry tetrahydrofuran (50 ml) was cooled to −78° C. under argon, and a solution of diisobutyl aluminum hydride in toluene (30 ml of 1M) was added dropwise. The mixture was stirred at −78° C. for 1.5 hours, then allowed to slowly warm to room temperature. The reaction was quenched by pouring onto iced dilute acetic acid, the product was extracted into methylene chloride and the organic extracts were washed with water, 5% sodium carbonate solution and brine. The dried, concentrated product was a light tan solid (3.32 g). Crystallization from ethanol/water gave 1-(2-chlorophenyl)methyl-5-hydroxymethyl-2-propylthio-1H-imidazole; mp 98°-101° C.

The title compound was prepared by the procedure of Example 1(iii and iv) using 1-(2-chlorophenyl)methyl-5-hydroxymethyl-2-propylthio-1H-imidazole in place of 2-n-butyl-1-(2-chlorophenyl)methyl-5-hydroxymethyl-1H-imidazole; mp 161°-162° C.

EXAMPLE 47

(E)-3-[{1-(2-Chorophenyl)methyl}-2-propenylthio-1H-imidazol-5-yl]-2-(2-thienyl)methyl-2-propenoic Acid The title compound is prepared following the procedure of Example 46 using allyl bromide in place of propyl bromide.

EXAMPLE 48

(E)-3-[{1-(2-Chorophenyl)methyl}-2-pentylthio-1H-imidazol-5-yl]-2-(2-thienyl)methyl-2-propenoic Acid The title compound is prepared following the procedure of Example 46 using 1-bromopentane in place of propyl bromide.

EXAMPLE 49

(E)-3-[{1-(2-Chorophenyl)methyl}-2-benzylthio-1H-imidazol-5-yl]-2-(2-thienyl)methyl-2-propenoic Acid The title compound is prepared following the procedure of Example 46 using benzyl bromide in place of propyl bromide.

EXAMPLE 50

(E)-3-[{1-(2-Chorophenyl)methyl}-2-cyclohexylthio-1H-imidazol-5-yl]-2-(2-thienyl)methyl-2-propenoic Acid The title compound is prepared following the procedure of Example 46 using cyclohexyl bromide in place of propyl bromide.

EXAMPLE 51

(E)-3-[{1-(2-Chorophenyl)methyl}-2-heptylthio-1H-imidazol-5-yl]-2-(2-thienyl)methyl-2-propenoic Acid The title compound is prepared following the procedure of Example 46 using 1-bromoheptane in place of propyl bromide.

EXAMPLE 52

(E)-3-[{1-(2-Chorophenyl)methyl}-2-hexenylthio-1H-imidazol-5-yl]-2-(2-thienyl)methyl-2-propenoic Acid The title compound is prepared following the procedure of Example 46 using 6-bromo-1-hexene in place of propyl bromide.

EXAMPLE 53

(E)-3-[{1-(2-Chorophenyl)methyl}-2-cyclopropylthio-1H-imidazol-5-yl]-2-(2-thienyl)methyl-2-propenoic Acid The title compound is prepared following the procedure of Example 46 using cyclopropyl bromide in place of propyl bromide.

EXAMPLE 54

(E)-3-[2-n-Butyl-1-{[2-chloro-4-(1H-tetrazol-5-yl]phenyl]methyl}-1H-imidazol-5-yl]-2-(2-thienyl)-methyl-2-propenoic Acid The procedure of Example 42 is followed using t-butyl 4-bromomethyl-3-chlorobenzoate (prepared from 3-chloro-4-methylbenzoic acid by esterification with 2-methylpropene in the presence of concentrated sulfuric acid, followed by methyl bromination with N-bromosuccinimide) in place of ethyl 4-bromomethyl-3-chlorobenzoate to give ethyl (E)-3-[2-n-butyl-1-{[2-chloro-4-(carbo-t-butoxy)phenyl]methyl}-1H-imidazol-5-yl]-2-(2-thienyl)methyl-2-propenoate. The t-butyl ester is converted to the corresponding acid compound using trifluoroacetic acid.

To a suspension-of ethyl (E)-3-[2-n-butyl-1-{(2-chloro-4-carboxyphenyl)methyl}-1H-imidazol-5-yl]-2-(2-thienyl)-methyl-2-propenoate in benzene is added thionyl chloride. The resultant mixture is heated to 50° C. for 90 minutes, then evaporated to an oily residue. The residue is taken up in hexane and evaporated again. The acid chloride is treated with concentrated ammonium hydroxide and then the reaction mixture is stirred for 16 hours at room temperature. The solid is filtered, washed with water, and dried at 50° C. under vacuum to yield the primary amide derivative.

To a solution of dimethylformamide in aceto-nitrile is added oxalyl chloride at 0° C. under argon. After 3 minutes, a solution of the amide prepared above in dimethylformamide is added via a cannula. Five minutes later, pyridine is added; the reaction mixture is stirred for an additional 5 minutes at 0° C. then partitioned between ethyl acetate and 50% aqeuous ammonium chloride. The ethyl acetate layer is washed with water and brine. The ethyl acetate extract is dried with anhydrous sodium sulfate and evaporated to give the corresponding nitrile derivative.

Tetrahydrofuran is added under argon with stirring to a mixture of the nitrile prepared above and aluminum chloride. Sodium azide is added all at once, followed by a tetrahydrofuran rinse, and the reaction is heated to 65° C. for 22 hours, then cooled to room temperature. The reaction mixture is diluted with ethyl acetate and treated with 10% hydrochloric acid solution with vigorous stirring for 5 minutes. The ethyl acetate layer is washed with water and brine. The ethyl acetate layer is dried with anhydrous sodium sulfate and evaporated to give ethyl (E)-3-[2-n-butyl-1-{[2-chloro-4-(1H-tetrazol-5-yl)phenyl]methyl}-1H-imidazol-5-yl]-2-(2-thienyl)-methyl-2-propenoate.

The title propenoic acid compound is prepared from the above ethyl ester by basic hydrolysis using aqueous base in methanol.

EXAMPLE 55

(E)-[2-n-Butyl-1-{(2-nitrophenyl)methyl}-1H-imidazol-5-yl]-2-(2-thienyl)methyl-2-propenoic Acid The title compound was prepared following the procedure of Example 1 using 2-nitrobenzyl bromide in place of 2-chlorobenzyl bromide; mp 205°–206° C.

EXAMPLE 56

(E)-[2-n-Butyl-1-{(3-nitrophenyl)methyl}-1H-imidazol-5yl]-2-(2-thienyl)methyl-2-propenoic Acid The title compound was prepared following the procedure of Example 1 using 3-nitrobenzyl alcohol in place of 2-chlorobenzyl alcohol; mp 182°–184° C.

EXAMPLE 57

(E)-[2-n-Butyl-1-{(4-nitrophenyl)methyl}-1H-imidazol-5-yl]-2-(2-thienyl)methyl-2-propenoic Acid The title compound was prepared following the procedure of Example 42 using 4-nitrobenzyl bromide in place of ethyl-4-bromomethyl-3-chlorobenzoate; mp 198°–200° C.

EXAMPLE 58

(E)-[2-n-Butyl-1-{(2-trifluoromethylphenyl)methyl}-1H-imidazol-5-yl]-2-(2-thienyl)methyl-2-propenoic Acid The title compound was prepared following the procedure of Example 1 using 2-trifluoromethylbenzyl alcohol in place of 2-chlorobenzyl alcohol; mp 202°–203° C.

EXAMPLE 59

(E)-[2-n-Butyl-1-{(2,3-dichlorophenyl)methyl}-1H-imidazol-5-yl]-2-(2-thienyl)methyl-2-propenoic Acid The title compound was prepared following the procedure of Example 1 using 2,3-dichlorobenzyl alcohol in place of 2-chlorobenzyl alcohol; mp 184°–185° C.

EXAMPLE 60

(E)-[2-n-Butyl-1-{(3-methoxy-2-nitrophenyl)methyl}-1H-imidazol-5-yl]-2-(2-thienyl)methyl-2-propenoic Acid The title compound was prepared following the procedure of Example 42 using 3-methoxy-2-nitrobenzyl bromide in place of ethyl 4-bromomethyl-3-chlorobenzoate; mp 213°–215° C.

EXAMPLE 61

(E)-[2-n-Butyl-1-{(2-cyanophenyl)methyl}-1H-imidazol-5-yl]-2-{2-thienyl)methyl-2-propenoic Acid The title compound was prepared following the procedure of Example 1 using 2-cyanobenzyl bromide in place of ethyl 4-bromomethyl-3-chlorbenzoate; mp 210°–212° C.

EXAMPLE 62

(E)-[2-n-Butyl-1-{(4-methoxy-3-methylphenyl)methyl}-1H-imidazol-5-yl]-2-(2-thienyl)methyl-2-propenoic Acid The title compound was prepared following the procedure of Example 42 using 4-methoxy-3-methylbenzyl bromide in place of ethyl 4-bromomethyl-3-chlorobenzoate; mp 140°–141° C.

EXAMPLE 63

(E)-[2-n-Butyl-1-{(3-methoxyphenyl)methyl}-1H-imidazol-5-yl]-2-(2-thienyl)methyl-2-propenoic Acid The title compound was prepared following the procedure of Example 1 using 3-methoxybenzyl alcohol in place of 2-chlorobenzyl alcohol; mp 170°–171° C.

EXAMPLE 64

(E)-[2-n-Butyl-1-{(2-methoxyphenyl)methyl}-1H-imidazol-5-yl]-2-(2-thienyl)methyl-2-propenoic Acid The title compound was prepared following the procedure of Example 1 using 2-methoxybenzyl alcohol and methanesulfonic anhydride in place of 2-chlorobenzyl alcohol and triflic anhydride; mp 186°–187° C.

EXAMPLE 65

(E)-[2-n-Butyl-1-{(2-hydroxyphenyl)methyl}-1H-imidazol-5-yl]-2-(2-thienyl)methyl-2-propenoic Acid The title compound was prepared from the 2-methoxy compound prepared in Example 64 using boron tribromide in methylene chloride; 181°–183° C.

EXAMPLE 66

(E)-[2-n-Butyl-1-{(2-chlorophenyl)methyl}-1H-imidazol-5-yl]-2-(5-methoxy-2-thienyl)methyl-2-propenoic Acid The title compound was prepared by the procedure of Example 1 using 3-(5-methoxy-2-thienyl)-2-phosphonopropionate in place of 3-(2-thienyl)-2-phosphonopropionate; mp 184°–185.5° C.

EXAMPLE 67

(E)-[2-n-Butyl-1-{(2-chlorophenyl)methyl}-1H-imidazol-5-yl]-2-(4-methoxy-2-thienyl)methyl-2-propenoic Acid The title compound was prepared by the procedure of Example 1 using 3-(4-methoxy-2-thienyl)-2-phosphonopropionate in place of 3-(2-thienyl)-2-phosphonopropionate; mp 170°–171° C.

EXAMPLE 68

(E)-3-[2-n-Hexyl-1-{(4-carboxyphenyl)methyl}-1H-imidazol-5-yl]-2-(2-thienyl)methyl-2-propenoic Acid The title compound was prepared following the procedure of Example 1, using caproylamidine methyl ether hydrochloride in place of valeramidine methyl ether hydrochloride and using 4-carbomethoxybenzyl alcohol in place of 2-chlorobenzyl alcohol; mp 210°–212° C.

EXAMPLE 69

(E)-3-[2-n-Propyl-1-{(2-nitrophenyl)methyl}-1H-imidazol-5-yl]-2-(2-thienyl)methyl-2-propenoic Acid The title compound was prepared following the procedure of Example 1 using butyramidine methyl ether hydrochloride in place of valeramidine methyl ether hydrochloride and 2-nitrobenzyl alcohol in place of 2-chlorobenzyl alcohol; mp 223° C.

EXAMPLE 70

(E)-3-[2-n-Butyl-1-{(2-chlorophenyl)methyl}-1H-imidazol-5-yl]-2-[1-phenyl-1-(2-thienyl)phenylmethyl]-2-propenoic Acid The title compound was prepared using the procedure of Example 1 (i, ii, iii, iv [Method B]) replacing methyl 3-(2-thienyl)propanoate with methyl 3-phenyl-3-(2-thienyl)propanoate [prepared as in Tetra. 44(7) 2055 (1988)]; mp 204°–206° C.

EXAMPLE 71

(E)-3-[2-n-Butyl-1-{(2-chlorophenyl)methyl}-1H-imidazol-5-yl]-2-[2-phenyl-1-(2-thienyl)ethyl]-2-propenoic Acid The title compound was prepared using the procedure of Example 1 (i, ii, iii, iv [Method B]) replacing methyl 3-(2-thienyl)propanoate with methyl 3-benzyl-3-(2-thienyl)propanoate [prepared following the procedure described in Tetra. 44 (7) 2055 (1988)]; mp 200°–202° C.

EXAMPLE 72

(E)-3-[2-n-Butyl-1-{(2-chlorophenyl)methyl}-1H-imidazol-5-yl]-2-{1-(2-thienyl)pentyl}-2-propenoic Acid The title compound was prepared using the procedure of Example 1 (i, ii, iii, iv [Method B]) replacing methyl 3-(2 -thienyl) propanoate with methyl 3-(2-thienyl)heptanoate; mp 161°–163° C.

EXAMPLE 73

E-3-[2-n-Butyl-1-{(2-carboxyphenyl)methyl}-1H-imidazol-5-yl]-2-(2-thienyl)methyl-2-propenoic Acid The title compound was prepared using the procedure of Example 42 replacing ethyl 4-bromomethyl-3-chlorobenzoate with ethyl 2-bromomethylbenzoate; 201°–202° C.

EXAMPLE 74

E-3-[2-n-Butyl-1-{(3-carboxyphenyl)methyl}-1H-imidazol-5-yl]-2-(2-thienyl)methyl-2-propenoic Acid The title compound was prepared by the procedure of Example 1 (iv, Method B) using 2-n-butyl-1-[(4-carbomethoxyphenyl)methyl]imidazole-5-aldehyde (prepared by the method described for the preparation of 2-n-butyl-1-[(4-carboethoxy-2-chlorophenyl)methyl]imidazole-5-aldehyde in Example 42) and methyl 3-(2-thienyl)propanoate; mp 243°–244° C.

EXAMPLE 75

(E)-3-[2-n-Butyl-1-{(4-hydroxy-3-methylphenyl)methyl}-1H-imidazol-5-yl]-2-(2-thienyl)methyl-2-propenoic Acid The title compound was prepared by demethylation of (E)-2-n-butyl-1-{(4-methoxy-3-methylphenyl)methyl}-1H-imidazol-5-yl]-2-(2-thienyl)methyl-2-propenoic acid, prepared in Example 62, using boron tribromide in methylene chloride; mp 150°–152° C.

EXAMPLE 76

(E)-3-[2-n-Butyl-1-{(4-carbomethoxyphenyl)methyl}-1H-imidazol-5-yl]-2-(2-thienyl)methyl-2-propenoic Acid The title compound was prepared using 2-n-butyl-1-[(4carbomethoxyphenyl)methyl]imidazole-5-aldehyde (prepared by the method described for the preparation of 2-n-butyl-1-[(4-carboethoxy-2-chlorophenyl)methyl-]imidazole-5-aldehyde in Example 42) and t-butyl 3-(2-thienyl)-propanoate by the procedure of Example 1 (iv, Method B), except, instead of basic hydrolysis, trifluoroacetic acid hydrolysis of the t-butyl ester was employed; mp 217°–220° C.

EXAMPLE 77

(E)-3-[2-n-Butyl-1-{(4-cyanophenyl)methyl}-1H-imidazol-5-yl]-2-(2-thienyl)methyl-2-propenoic Acid The title compound was prepared using 2-n-butyl-[(4cyanophenyl)methyl]imidazole-5-aldehyde (prepared by the method of Example 42 describing the preparation of 2-n-butyl-1-[(4-carboethoxy-2-chlorophenyl)methyl]imidazole-5-aldehyde) and methyl 3-(2-thienyl)propanoate by the procedure of Example 1 (iv, Method B), except, instead of basic hydrolysis of the ester with sodium hydroxide, potassium carbonate hydrolysis was employed; mp 190°–192° C.

EXAMPLE 78

(E)-3-[2-n-Butyl-1-{(4-carbamoylphenyl)methyl}-1H-imidazol-5-yl]-2-(2-thienyl)methyl-2-propenoic Acid Methyl (E)-3-[2-n-butyl-1-{(4-cyanophenyl)methyl}-1H-imidazol-5-yl]-2-(2-thienyl)methyl-2-propanoate, prepared in Example 77, was subjected to hydrolysis with concentrated hydrochloric acid to give the title compound; mp 210°–212° C.

EXAMPLE 79

(E)-3-[2-n-Butyl-1-{[4-(1H-tetraol-5-yl)-phenyl]methyl}-1H-imidazol-5-yl]-2-(2-thienyl)-methyl-2-propenoic Acid The title compound was prepared from methyl (E)-3-[2-n-butyl-1-{(4-cyanophenyl)methyl}-1H-imidazol-5yl]-2-(2-thienyl)methyl-2-propanoate, prepared in Example 77, using the procedure described in Example 54; mp 246°–248° C.

EXAMPLE 80

(E)-3-[2-n-Propyl-1-{(4-carboxyphenyl)methyl}-1H-imidazol-5-yl]-2-(2-thienyl)methyl-2-propenoic Acid The title compound was prepared using the procedure of Example 1 replacing valermamidine methyl ether hydrochloride with butyramidine methyl ether hydrochloride and replacing 2-chlorbenzyl alcohol with 4-carbomethoxybenzyl alcohol; mp 250° C. (d).

EXAMPLE 81

(E)-3-[2-n-Propyl-1-{(2-chlorophenyl)methyl}-1H-imidazol-5-yl]-2-(2-thienyl)methyl-2-propenoic Acid The title compound was prepared using the procedure of Example 1 replacing valeramidine methyl ether hydrochloride with butyramidine methyl ether hydrochloride; mp 200° C.

EXAMPLE 82

(E)-3-[2-n-Hexyl-1-{(2-chlorophenyl)methyl}-1H-imidazol-5-yl]-2-(2-thienyl)methyl-2-propenoic Acid The title compound was prepared using the procedure of Example 1 replacing valeramidine methyl ether hdyrochloride with caproylamidine methyl ether hydrochloride; mp 161°–163° C.

EXAMPLE 83

(E)-3-[2-n-Butyl-1-{(4-carboxy-2,3-dichlorophenylmethyl}1H-imidazol-5-yl]-2-(2-thienyl)methyl-2-propenoic Acid (i) methyl 2,3-dichloro-4-methylbenzoate Chlorine was bubbled into a suspension of 17.2 g of ferric chloride in 1516 g of p-xylene until the mixture contained 40.5% 2-chloro-1,4-xylene, 43% 2 5-dichloro-1,4-xylene, and 16.5% 2,3-dichloro-1,4-xylene as monitored by gas chromatography. Distillation at 15 mmHg gave 710 g of a fraction with a boiling point of 95°–106° which was 30–40% 2,3-dichloro-1,4-xylene. Trituration with isopropanol followed by concentration of the isopropanol solution gave 360 g of product which contained 45% of 2,3-dichloro-1,4-xylene. Reflux of 251 g of this with 3.5 liters of 45% nitric acid for 23 hours followed by quenching in 3 liters of ice water gave a solid which was dissolved in 6.4% aqueous potassium hydroxide solution. This was extracted twice with ethyl acetate. Acidification of the aqueous solution gave a solid which was dissolved in 3200 mL of methanol containing 50 mL of concentrated sulfuric acid and refluxed for 18 hours. The reaction mixture was concentrated under vacuum, diluted with water, and extracted with ethyl acetate. Concentration gave an oil which still contained some acid so the esterification was repeated to give 198 g of mixed esters (39% 2,5-dichloro- and 52% 2,3-dichloro-1,4-xylene). Repeated chromatography (silica gel, mobile phase 80:20 hexanemethylene chloride) of the crude mixture gave 53 g of material which contained 98% of methyl 2,3-dichloro-4-methylbenzoate.

(ii) methyl 4-bromomethyl-2,3-dichlorobenzoate

A mixture of 40 g (0.183 mol) of methyl 2,3-dichloro-4-methylbenzoate, 34.17 g (0.192 mol) of N-bromosuccinimide, 0.4 g (0.0017 mol) of benzoylperoxide, and 640 mL of carbon tetrachloride was stirred at room temperature while being irradiated with a 150 watt flood lamp for 2.5 hours. Concentration of the filtered reaction mixture under vacuum gave 54 g of material which on trituration with pentane followed by storage of the slurry at 5° C. for 18 hours gave 34.6 g (63.5%) of product; mp 57°–61° C.

(iii) methyl 4-[(2-butyl-5-formyl-4-iodo-1H-imidazol-1-yl)methyl]-2,3-dichlorobenzoate A suspension of 26.7 g (0.096 mol) of 2-butyl-4-iodoimidazole-5-carboxaldehyde (prepared in Example 96 (i) and (ii)) and 28.01 g (0.203 mol) of dry potassium carbonate in 350 mL of dimethylformamide was stirred under argon for 20 minutes. Then 30 g (0.10 mol) of methyl 4-bromothyl-2,3-dichlorobenzoate was added and the mixture was stirred at 80° C. for 1.5 hours. The reaction mixture was poured into water and extracted several times with ether. Filtration of the solid formed at the ether-water interface gave 19.35 g of product. The ether layer was washed 4 times with water, once with brine, and then concentrated under vacuum to give a solid. Recrystallization of the combined solids from methanol gave 32.55 g (68%) of product; mp 135°–137° C.

(iv) methyl 4-[(2-butyl-5-formyl-1H-imidazol-1-yl)methyl]-2,3-dichlorobenzoate

A suspension of 34.2 g (0.069 mol) of methyl 4-[(2-butyl-5-formyl-4-iodo-1H-imidazol-1-yl)methyl]-2,3-dichlorobenzoate and 6.84 g of 10% palladium on carbon in 850 mL of ethyl acetate was shaken under hydrogen at 3 Torr for 1 hour. The mixture was filtered through Celite® and concentrated under vacuum to 300 mL. This solution was washed in turn with 5% sodium carbonate solution, water, and brine and then concentrated to an oil which crystallized on standing. This was dissolved in 25 mL of hot methanol which when cooled gave crystals. The suspension was slowly diluted with water and then filtered to give 24.39 g (96%) of crystals; mp 94°–96° C.

(v) methyl (E)-3-[2-n-butyl-1-{(4-carbomethoxy-2,3-dichlorophenyl)methyl}-1H-imidazole-5-yl]-2-(2-thienyl)methyl-2-propanoate A mixture of 19.0 g (0.051 mol) of methyl 4-[(2-butyl-5-formyl-1H-imidazol-1-yl)methyl]-2,3-dichlorobenzoate 47.6 g (0.208 mol) of 2-carbethoxy-3-thienylpropionic acid, 2.19 g (0.026 mol) of piperidine, and 900 mL of benzene was heated under reflux for 18 hours using a Dean-Stark trap to remove water. An additional 13.33 g (0.058 mol) of the thienylpropionic acid was added and the refluxing was continued for 5 hours; another 26.6 g (0.116 mol) of ester and 1 mL of piperidine was added and the refluxing continued for an additional 18 hours. Concentration of the reaction mixture under vacuum gave a syrup which was dissolved in ether and then made acidic with ethereal hydrochloric acid. The resulting solid was collected by filtration and washed with ether to give 20.05 g (68%) of crystals; mp 165°–166°.

(vi) (E)-3-[2-n-butyl-1-{(4-carboxy-2,3-dichlorophenyl)methyl}-1H-imidazol-5-yl]-2-(2-thienyl)-methyl-2-propanoic acid A mixture of 19.5 g (0.034 mol) of methyl(E)-3-[2-n-butyl-1-{(4-carbomethoxy-2,3-dichlorophenyl)methyl}-1H-imidazole-5-yl]-2-(2-thienyl)methyl-2-propanoate and 9.60 g (0.24 mol) of sodium hydroxide, 100 mL of ethanol and 100 mL of eater was heated on a steam bath to form a homogeneous solution which was then stirred at 25° C. for 18 hours. The mixture was concentrated on a steam bath to 100 mL, filtered, and diluted with 150 mL of water. The pH was brought to 3.38 with 10% hydrochloric acid solution. The resulting solid was collected by filtration. The solid was suspended in 350 mL of acetone which was heated to reflux and 200 mL of water was added slowly. The mixture concentrated to 300 mL. Chilling and filtration gave a solid which was washed with water and dried at 90° C. under vacuum (0.5 mmHg) to give 15.35 g (91%) of the title compound; mp 245°–247° C.

EXAMPLE 84

(E)-3-[2-n-Butyl-1-{(4-carboxy-2,5-dichlorophenyl)methyl}-1H-imidazol-5-yl]-2-(2-thienyl)methyl-2-propenoic Acid The title compound was prepared using the procedure of Example 42 replacing ethyl 4-bromomethyl-3-chlorobenzoate with methyl 4-bromomethyl-3,6-dichlorobenzoate (prepared by oxidation of 2,5-dichloro-p-xylene with nitric acid, followed by esterification with methanol/hydrochloric acid, and methyl bromination with N-bromosuccinimide); mp 145° C.

EXAMPLE 85

(E)-3-[2-n-Butyl-1-{(4-carboxynaphth-1-yl)methyl-1H-imidazol-5-yl]-2-(2-thienyl)methyl-2-propenoic Acid (i) 2-butyl-5-hydroxymethyl-4-iodoimidazole N-Iodosuccinimide (148.75 g, 0.661 mol) was added to a stirred solution of 2-butyl-4-hydroxymethylimidazole (100.78 g, 0.652 mol) in 500 mL of absolute ethanol. After 20 minutes the solution was heated to 40°–45° C. for 45 minutes, diluted with 2.5 liters of water, and chilled. The crystalline product was collected by filtration, washed with water, and dried to give 174.5 g (95%) of crystals; mp 166°–166.5° C.

(ii) 2-butyl-4-iodoimidazol-5-carboxaldehyde

A stirred mixture of 174.1 g (0.62 mol) of 2-butyl-5-hydroxymethyl-4-iodoimidazole and 360 g (4.14 mol) of manganese dioxide in 3 liters of methylene chloride was refluxed for 24 hours using a trap to remove water. The hot reaction mixture was filtered through Celite® which was then washed with 4.5 liters of boiling methylene chloride. The combined filtrates were concentrated to dryness, the residue was dissolved twice in 150 mL of methanol and the solution was concentrated to dryness. The residue was dissolved in 130 mL of methanol and chilled. After crystallization had occurred, 700 mL of water was added slowly. The mixture was chilled, the solid was collected by filtration, and washed with water to give 145.2 g (84%) of product; mp 104°–105° C.

(iii) methyl-4-[(2-butyl-5-formyl-4-iodo-1H-imidazol-1-yl)methyl]naphthalene-1-carboxylate A suspension of 29.53 g (0.214 mol) of powdered potassium carbonate, 60.00 g (0.214 mol) of 2-butyl-4-iodoimidazole-5-carboxaldehyde and 65.68 g (0.235 mol) of methyl 4-bromomethylnaphthalene-1-carboxylate (E. A. Dixon, A. Fischer, and F. P. Robinson, *Can. J. Chem*, 59, 2629 (1981)) in 600 mL of dimethylformamide was stirred for 5 hours under argon at 70° C. An additional 6.56 g (0.0235 mol) of the bromomethyl ester was added and the suspension was stirred an additional 15 hours at 70° C. The reaction mixture was poured into water and the resulting solid was collected by filtration, washed with water, and triturated several times with 250 mL of boiling methanol to give 86.8 g (85%) of a solid; mp 177.5°–179° C.

(iv) methyl-4-[(2-butyl-5-formyl-1H-imidazol-1-yl)-methyl]naphthalene-1-carboxylate A suspension of 40.0 g (83.9 mmol) of methyl-4-[(2-Butyl-5-formyl-4-iodo-1H-imidazol-1-yl)methyl]naphthalene-1-carboxylate, 9.07 g (92.4 mmol) of potassium acetate, and 6.0 g of 10% palladium on carbon in 1.2 liters of ethyl acetate was hydrogenated for 2 hours. The solids were removed by filtration and an additional 8.0 g of 10% palladium on carbon and 9.01 g (92.4 mmol) of potassium acetate was added. After hydrogenating the reation mixture an additional 2 hours, the solids were removed by filtration and the solution was concentrated to about ⅓ volume. The ethyl acetate solution was washed with aqueous sodium carbonate solution, dried over magnesium sulfate, and concentrated under vacuum to give an oil which crystallized. Recrystallization from methylene chloride-hexane gave 25.77 g (87.6%) of colorless crystals; mp 95.5°–97° C.

(v) methyl (E)-3-[2-n-butyl-1-{(4-carbomethoxynaphth-1-yl)methyl}-1H-imidazol-5-yl]-2-(2-thienyl)methyl-2-propenoate The title compound from 25.0 g of methyl-4-[(2-Butyl-5-formyl-1H-imidazol-1-yl)-methyl] naphthalene-1-carboxylate the procedure of Example 20 to give 22.12 g (56%) of product as the hydrochloride salt; mp 217°–218° C.

(vi) (E)-3-[[2-n-butyl-1-{(4-carboxynaphth-1-yl)methyl}-1H-imidazol-5-yl]-2-(2-thienyl)methylpropenoic acid A slurry containing 14.46 g (26.14 mmol) of methyl (E)-3-[2-n-butyl-1-{(4-carbomethoxynaphth-1-yl) methyl}-1H-imidazol-5-yl]-2-(2-thienyl)methyl-2-propenoate, 8.38 g (2.09 mmol) of potassium hydroxide in a mixture of 165 mL of ethanol and 85 mL of water was stirred at ambient temperature for 18 hours. Concentration under vacuum and dilution with water gave 400 mL of a clear solution. Adjustment of the pH to 4.03 with hydrochloirc acid gave crystals which when re-crystallized from methanol gave 9.89 g (80%) of colorless crystals; mp 218°–219° C. as a partial hydrate.

EXAMPLE 86

(E)-3-[2-n-Butyl-1-{(2,3-dichlorophenyl)methyl}-1H-imidazol-5-yl]-2-(2-thienyl)methyl-2-propenamide (E)-3-[2-n-Butyl-1-{(2,3-dichlorophenyl)methyl-1H-imidazol-5-yl]-2-(2-thienyl)methyl-2-propenoic acid, prepared in Example 59, was treated with thionyl chloride and then ammonium hydroxide, as described in Example 54, to give the title compound; mp 185°–187° C.

EXAMPLE 87

(E)-3-[2-n-Butyl-1-{(4-carbamoylphenyl)methyl}-1H-imidazol-5-yl]-2-(2-thienyl)methyl-2-propenamide (E)-3-[2-n-Butyl-1-{(4-carboxyphenyl)methyl}-1H-imidazol-5-yl]-2-(2-thienyl)methyl-2-propenoic acid, prepared in Example 41, was treated with thionyl chloride and then ammonium hydroxide, as described in Example 54, to give the title compound; mp 204°–206° C.

EXAMPLE 88

(E)-3-[2-n-Butyl-1-{(2-nitrophenyl)methyl}-1H-imidazol-5-yl]-2-(2-thienyl)methyl-2-propenamide (E)-3-[2-n-Butyl-1-{(2-nitrophenyl)methyl}-1H-imidazol-5-yl]-2-(2-thienyl)methyl-2-propenoic acid, prepared in Example 55, was treated with thionyl chloride and then ammonium hydroxide, as described in Example 54, to give the title compound; mp 183°–185° C.

EXAMPLE 89

E-3-[2-n-Butyl-1-{(2-chlorophenyl)methyl}-1H-imidazol-5-yl]-2-(2-thienyl)-methyl-2-propenoxy Acetic Acid To a suspension of sodium hydride (53 mg, 2.3 mmol) in 5 mL of glyme was added portionwise (E)-3-[2-n-butyl-1-{(2-chlorophenyl) methyl}-1H-imidazol-5-yl]-2-(2-thienyl)methyl-2-propenol (0.802 mg, 2.0 mmol, prepared as described in Example 17). After stirring for 30 minutes, methyl bromoacetate (3.35 mg, 2.2 mmol) was added dropwise. The reaction was stirred overnight at room temperature and then the mixture was poured into ice-water. The product was extracted into ethyl acetate (3×). The combined organic extracts were washed with water and brine and dried with anhydrous magnesium sulfate. The solvent was removed in vacuo. The residue was chromatographed on silica gel eulting with hexane/ethyl acetate (4:6) to give 2.44 mg (26%) of the ester of the title compound as an oil.

The ester was saponified by base as described in Example 1, iv, Method A(c); mp 141°–142° C. (ethyl acetate/methanol).

EXAMPLE 90

E-3-[2-n-Butyl-1-{(2-chlorophenyl)methyl}-1H-imidazol-5-yl]-2-(2-thienyl)methyl-2-propenyl Glycine To a solution of (E)-3-[2-n-butyl-1-{(2-chlorophenyl)methyl-1H-imidazol-5-yl]-2-(2-thienyl)methyl-2-propenoic acid (0.5 g, 1.2 mmol prepared in Example 1) intetrahydrofuran (12 mL) was added N-hydroxysuccinimide (0.153, 1.33 mmol), followed by dicyclohexylcarbodiimide (0.249 g, 1.2 mmol) in 5 mL of tetrahydrofuran. The reaction mixture was heated at 35° C. for one hour and then glycine methyl ester hydrochloride (0.197 g, 1.57 mmol) and triethylamine (0.22 mL, 1.57 mmol) were added. The reaction was stirred at room temperature overnight. The mixture was diluted with 20 mL of ethyl acetate and the solids were filtered. The filtrate was concentrated to dryness and the residue was chromatographed on silica gel eluting with ethy acetate/hexane (4:6) to give 0.258 g (44%) of the esteramide as an oil.

The ester was saponified to the title acid compound by base, as described in Example 1 (iv, Method A(c); mp 175°–177° C.

EXAMPLE 91

(E)-3-[2-n-Butyl-1-{(2-chlorophenyl)methyl}-1H-imidazol-5-yl]-2-(2-thienyl)methyl-2-propenamide (E)-3-[2-n-Butyl-1-{(2-chlorophenyl)methyl}-1H-imidazol-5-yl]-2-(2-thienyl)methyl-2-propenoic acid, prepared in Example 1, was treated with thionyl chloride and then ammonium hydroxide, as described in Example 54, to give the title compound; mp 184°–185° C.

EXAMPLE 92

(E)-3-[2-n-Butyl-1-{(2-trifluoromethylphenyl)methyl}-1H-imidazol-5-yl]-2-(2-thienyl)methyl-2-propenamide (E)-3-[2-n-Butyl-1-{(2-trifluoromethylphenyl)-methyl-1H-imidazol-5-yl]-2-(2-thienyl)methyl-2-propenoic acid, prepared in Example 58, was treated with thionyl chloride and then ammonium hydroxide, as described in Example 54, to give the title compound; mp 207°–208° C.

EXAMPLE 93

Ethyl (E)-3-[2-n-butyl-1-{(4-carbomethoxyphenyl)methyl}-1H-imidazol-5-yl]-2-(2-thienyl)methyl-2-propanoate The title compound was prepared following the procedure of Example 1 (iv, Method B) using 2-n-butyl-1-[(4-carbomethoxyphenyl)methyl]imidazole-5-aldehyde, prepared by the method described for the preparation of 2-n-butyl-1-[(4-carboethoxy-2-chlorophenyl)methyl-]imidazole-5-aldehyde in Example 42, and ethyl 3-(2-thienyl)propanoate; mp 130°–132° C.

EXAMPLE 94

(E)-3-[2-n-Butyl-1-{(4-carboxyphenyl)ethyl}-1H-imidazo-5-yl]-2-(2-thienyl)methyl-2-propenoic Acid The title compound was prepared following the procedure of Example 42, replacing 2-n-butyl-1-[(4-carboethoxy-2-chlorophenyl)methyl]imidazole-5-aldehyde with 2-n-butyl-1-[(4-carboethoxyphenyl)ethyl]imidazole-5-aldehyde; mp 256°-259° C.(d).

EXAMPLE 95

(E)-3-[2-n-Butyl-1-{4-carboxyphenyl}-1H-imidazo-5-yl]-2-(2-theinyl)methyl-2-propenoic Acid The title compound was prepared following the procedure of Example 42 replacing 2-n-butyl-1-[(4-carboethoxy-2-chlorophenyl)methy]imidazole-5-aldehyde with 2-n-butyl-[(4-carboethoxyphenyl]imidazole-5-aldehyde; mp 260°-265° C.(d).

EXAMPLE 96

(E)-3-[2-n-Butyl-1-{(3,4-dicarboxyphenyl)methyl}-1H-imidazol-5-yl]-2-(2-thienyl)methyl-2-propenoic Acid The title compound was prepared following the procedure of Example 20 replacing methyl 3-(4-pyridyl)propanoate with methyl 3-(2-thienyl)propanoate and 2-n-butyl-1-(2-chlorophenyl)methyl-1H-imidazol-5-carboxaldehyde with 2-n-butyl-1-(3,4-dicarbomethoxyphenyl) methyl}-1H-imidazol-5-carboxaldehyde; mp 204°-205° C.

EXAMPLE 97

(E)-3-[2-n-Butyl-1-{4-carboxyphenyl)methyl}-1H-imidazol-5-yl]-2-(2-thienyl)ethyl-2-propenoic Acid The title compound was prepared following the procedure of Example 20 replacing methyl 3-(4-pyridyl)-propanoate with methyl 4-(2-thienyl)butanoate and 2-n-butyl-1-(2-chlorophenyl)methyl-1H-imidazol-5-carboxaldehyde with 2-n-butyl-1-)4-carbomethoxyphenyl) methyl-1H-imidazol-5-carboxaldehyde; mp 244°-246° C.(d).

EXAMPLE 98

(E)-3-[2-n-Butyl-1-{(4-carboethoxyphenyl)methyl}-1H-imidazol-5-yl]-2-(2-thienyl)methyl-2-propenoic Acid The title compound was prepared following the procedure of Example 42 replacing 2-n-butyl-1-[(4-carbomethoxy-2-chlorophenyl)methyl]imidazole-5-aldehyde with 2-n-butyl-1-[(4-carboethoxyphenyl)methyl]imidazole-5-aldehyde ethyl 2-carboxy-3-(2-thienyl)-propionate and potassium hydroxide in water-ethanol at ambient temperature with lithium chloride in dimethylformamide at 80°-125° C.; mp 129°-131° C. (d).

EXAMPLE 99

(E)-3-[2-n-Butyl-1-{(4-carboxyphenyl)methyl}-1H-imidazol-5-yl]-2-(2-thienyl)methyl-2-propenyl. Glycine The title compound was prepared following the procedure of Example 90 replacing (E)-3-[2-n-butyl-1-{2-chlorophenyl)methyl}-1H-imidazol-5-yl]-2-(2-thienyl) methyl-2-propenoic acid with (E)-3-[2-n-butyl-1-{(4-carboethoxyphenyl)methyl}-1H-imidazol-5-yl]-2-(2-thienyl)methyl-2-propenoic acid, prepared in Example 98; mp 223°-224 ° C.

EXAMPLE 100

(E)-3-[2-n-Butyl-1-{(4-carboxymethylphenyl)methyl}-1H-imidazol-5-yl]-2-(2-thienyl)methyl-2-propenoic Acid The title compound was prepared following the procedure of Example 42 replacing ethyl 4-bromomethyl-3-chlorobenzoate with 4-bromomethylphenyl acetic acid, methyl ester; mp 169°-171° C.

EXAMPLE 101

(E)-3-[2-n-Butyl-1-{(4-carboxymethoxyphenyl)methyl}-1H-imidazol-5-yl]-2-(2-thienyl)methyl-2-propenoic Acid The title compound was prepared following the procedure of Example 42 replacing ethyl 4-bromomethyl-3-chlorobenzoate with 4-bromomethylphenoxyacetic acid, methyl ester; mp 192°-194° C.

EXAMPLE 102

(E)-3-[2-n-Butyl-1-{4-carboxy-3-hydroxyphenyl)methyl}-1H-imidazol-5-yl]-2-(2-thienyl)methyl-2-propenoic Acid (i) methyl 4-methylsalicylate To a suspension of 10 g (0.0651 mol) of 4-methylsalicylic acid in 150 mL of methanol was added 50 mL of ethereal hydrochloric acid. The reaction mixture was heated at 60° C. for 60 hours. The solvent was removed under vacuum. After adding hexane-ethyl acetate, the resulting solid was filtered and the filtrate was evaporated to give 10.2 g (94%) of product as an oil.

(ii) methyl 2-methoxymethoxy-4-methylbenzoate

To a suspension of sodium hydride (1.62 g, 0.0675 mol) in 90 mL of dimethylformamide was added dropwise a solution of methyl 4-methylsalicylate (10.2 g, 0.0614 mol) in 20 mL of diethyl ether. After stirring for 15 minutes, a solution of chloromethyl methyl ether (5.6 mL, 0.0737 mol) in 10 mL of diethyl ether was added. The reaction mixture was stirred at room temperature for 18 hours and then it was partitioned between water and diethyl ether. The layers were separated and the aqueous layer was extracted an additional three times with diethyl ether. The combined organic extracts were washed with brine, dried with magnesium sulfate, and concentrated in vacuo to give 14.5 g of an oil. The product was purified by flash chromatography on silica gel eluting with 10%-15% ethyl acetate in hexane to give 9.41 g (73%) of product as an oil.

(iii) methyl 4-bromomethyl-2-methoxymethoxybenzoate

To a solution of methyl 2-methoxymethoxy-4-methylbenzoate (9.41 g, 0.0448 mol) in 150 mL of carbon tetrachloride was added N-bromosuccinimide (7.97 g, 0.0448 mol) and benzoyl peroxide (0.45 g, 0.002 mol). The reaction mixture was refluxed for 18 hours. The solid was filtered and the filtrate was concentrated in vacuo to give 13.2 g of an oil. The product was purified by flash chromatography on silica gel eluting with 20% ethyl acetate in hexane to give 10.2 g (79%) of product as an oil.

(iv) 2-n-butyl-1-(4-carbomethoxy-3-methoxymethoxyphenylmethyl-4-chloro-1H-imidazol-5-carboxaldehyde To a solution of 2-n-butyl-4-chloro-1H-imidazol-5-carboxaldehyde (2.0 g, 10.7 mmol) in 25 mL of dimethylformamide was added potassium carbonate (1.78 g, 12.9 mmol). The suspension was stirred at 45° C. for 15 minutes and then methyl 4-bromomethyl-2-methoxymethoxybenzoate was added. The reaction mixture was stirred at 60° C. for 2 hours and then it was partitioned between ice water and ethyl acetate. The layers were separated and the aqueous layer was extracted a second time with ethyl acetate. The combined organic extracts were washed with brine, dried with magnesium sulfate, and concentrated in vacuo. The product was purified by flash chromatography on silica gel eluting with 30% ethyl acetate in hexane to give 3.28 g (78%) of product as an oil.

(v) 2-n-butyl-1-(4-carbomethoxy-3-methoxymethoxyphenyl)methyl-1-H-imidazol-5-carboxaldehyde To a suspension of 0.32 g of 10% palladium on carbon in 15 mL of methanol containing potassium acetate (0.813 g, 8.28 mmol) was added a solution of 2-n-butyl-1-(4-carbomethoxy-3-methoxymethoxyphenyl)methyl-4-chloro-1H-imidazol-5-carboxaldehyde (3.27 g, 8.28 mmol) in 60 mL of methanol. The reaction was hydrogenated at 4 psi for 40 minutes. The solid was filtered and the filtrate was concentrated in vacuo. The residue was partitioned between diethyl ether and water. The pH of the aqueous layer was adjusted to 7.5 with 5% sodium carbonate solution. The layers were separated and the organic layer was washed with brine and dried with magnesium sulfate. The solvent was removed in vacuo to give 2.59 g (87%) of product as an oil.

(vi) methyl (E)-3-[2-n-butyl-1-{(4-carbomethoxy-3-methoxymethoxyphenyl)methyl}-1H-imidazol-5-yl ]-2-(2-thienyl)methyl-2-propenoate The title compound was prepared following the procedures of Example 1, Method B, (a)–(c) replacing 2-n-butyl-1-(2-chlorophenyl)methyl-1H-imidazol-5-carboxaldehyde with 2-n-butyl-1-(4-carbomethoxy-3-methoxymethoxyphenyl)-methyl-1H-imidazol-5-carboxaldehyde. The product was isolated as an oil.

(vii) methyl (E)-3-[2-n-butyl-1-{(4-carbomethoxy-3-hydroxyphenyl)methyl}-1H-imidazol-5-yl]-2-(2-thienyl)methyl-2-propenoate To a solution of methyl (E)-3-[2-n-butyl-1-{(4-carbomethoxy-3-methoxymethoxyphenyl)methyl{-1H-imidazol-5-yl]-2-(2-thienyl)methyl-2-propenoate (2.1 g, 4.1 mmol) in 40 mL of methanol was added approximately 0.1 mL of concentrated hydrochloric acid. The reaction was refluxed for 5 hours and then concentrated in vacuo. The residue was partitioned between ethyl acetate and saturated sodium bicarbonate solution. The layers were separated. The organic extract was dried with magnesium sulfate, and the solvent was removed in vacuo to give 1.76 g (92%) of product as an oil.

(viii) (E)-3-[2-n-butyl-1-{(4-carboxy-3-hydroxyphenyl)methyl 1}-1H-imidazol-5-yl]-2-(2-thienyl)-methyl-2-propenoate The title compound was prepared following the procedure of Example 1, Method A (c); mp 192.5°–194° C.

EXAMPLE 103

(E)-3-[2-n-Butyl-3{2-carboxybiphenyl-5-yl)methyl}-1H-imidazol-5-yl]-2-(2-thienyl)methyl-2-propenoic Acid The title compound was prepared following the procedure of Example 102, using methyl 4-bromomethyl-2-phenylbenzoate in place of methyl 4-bromomethyl-2-methoxymethoxybenzoate; mp 158°–161° C. (hydrochloric acid salt).

EXAMPLE 104

(E)-3-[2-n-Butyl-1-{(4-carboxyethenylphenyl)methyl}-1H-imidazol-5-yl]-2-(2-thienyl)methyl-2-propenoic Acid The title compound was prepared following the procedure of Example 42 replacing 2-n-butyl-1-[(4-carboethoxy-2-chlorophenyl)methyl]imidazole-5-aldehyde with 2-n-butyl-1-[(4-carbomethoxyethenylphenyl)methyl]imidazole-5-aldehyde; mp 199°–203° C.

EXAMPLE 105

(E)-3-[2-n-Butyl-1-{(4-carboxyethylphenyl)methyl}-1H-imidazol-5-yl]-2-2-thienyl)methyl-2-propenoic Acid The title compound was prepared following the procedure of Example 42 replacing 2-n-butyl-1-[(4-carboethoxy-2-chlorophenyl)methyl]imidazole-5-aldehyde with 2-n-butyl-1-[(4-carbomethoxyethylphenyl)methyl]-1H-imidazole-5-aldehyde; mp 179°–182° C.

EXAMPLE 106

(E)-3-[2-(2-phenylethyl)-1-{(4-carboxyphenyl)methyl-1H-imidazol-5-yl]-2-(2-thienyl)methyl-2-propenoic Acid The title compound was prepared following the procedure of Example 1; mp 213.5°–214.5° C.

EXAMPLE 107

(E)-3-[2-(3-methylbutyl)-1-[(4-carboxyphenyl)methyl}-1H-imidazol-5-yl]-2-(2-thienyl)methyl-3-propenoic Acid The title compound was prepared following the procedure of Example 1; mp 251.5°–252° C.

EXAMPLE 108

An oral dosage form for administering orally active Formula (I) compounds is produced by screening, mixing and filling into hard gelatin capsules the ingredients in proportions, for example, as shown below.

| Ingredients | Amounts |
| --- | --- |
| (E)-3-[2-n-butyl-1-{(4-carboxyphenyl)methyl}-1H-imidazol-5-yl]-2-(2-thienyl)methyl-2-propenoic acid | 100 mg |
| magnesium stearate | 10 mg |
| lactose | 100 mg |

EXAMPLE 109

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| (E)-3-[2-n-butyl-1-{(4-carboxy-2-chlorophenyl)-methyl}-1H-imidazol-5-yl]-2-(2-thienyl)methyl-2-propenoic acid | 75 mg |
| calcium sulfate dihydrate | 100 mg |
| sucrose | 15 mg |
| starch | 8 mg |
| talc | 4 mg |

| Ingredients | Amounts |
|---|---|
| stearic acid | 2 mg |

EXAMPLE 110

(E)-3-[2-n-Butyl-1-{(4-carboxy-3-chlorophenyl)methyl}-1H-imidazol-5-yl]-2-(2-thienyl)methyl-2-propenoic acid, 50 mg, is dispersed in 25 mL of normal saline to prepare an injectable preparation.

EXAMPLE 111

A topical opthamological solution for administering Formula (I) compounds is produced by mixing under sterile conditions the ingredients in proportions, for example, as shown below.

| Ingredients | Amounts (mg/mL) |
|---|---|
| (E)-3-[2-n-butyl-1-{2-chlorophenyl)methyl}-1H-imidazol-5-yl]-2-(2-thienyl)methyl-2-propenoic acid | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s.ad 1.0 mL |
| 1.0 N sodium hydroxide | q.s.ad pH 7.4 |

It is to be understood that the invention is not limited to the embodiments illustrated hereabove and the right to the illustrated embodiments and all modifications coming within the scope of the following claims is reserved.

What is claimed is:

1. A compound which is (E)-3-[2-n-butyl-1-{(4-carboxynaphth-1-yl)methyl}-1H-imidazol-5-yl]-2-(2-thienyl)methyl-2-propenoic acid or a pharmaceutically acceptable salt thereof.

2. A pharmaceutical composition comprising a pharmaceutical carrier and (E)-3-[2-n-butyl-1-{(4-carboxynaphth-1-yl)methyl}-1H-imidazol-5-yl]-2-(2-thienyl)methyl-2-propenoic acid.

3. A method of antagonizing angiotensin II receptors which comprises administering to a subject in need thereof an effective amount (E)-3-[2-n-butyl-1-{(4-carboxynaphth-1-yl)methyl}-1H-imidazol-5-yl]-2-(2-thienyl)methyl-2-propenoic acid.

4. A method of treating hypertension which comprises administering to a subject in need thereof an effective amount of (E)-3-[2-n-butyl-1-{(4-carboxynaphth-1-yl)methyl}-1H-imidazol-5-yl]-2-(2-thienyl)methyl-2-propenoic acid.

5. A method of treating congestive heart failure which comprises administering to a subject in need thereof an effective amount of (E)-3-[2-n-butyl-1-{(4-carboxynaphth-1-yl)methyl}-1H-imidazol-5-yl]-2-(2-thienyl)methyl-2-propenoic acid.

6. A method of treating renal failure which comprises administering to a subject in need thereof an effective amount of (E)-3-[2-n-butyl-1-{(4-carboxynaphth-1-yl)methyl}-1H-imidazol-5-yl]-2-(2-thienyl)methyl-2-propenoic acid.

7. A method of treating glaucoma which comprises administering to a subject in need thereof an effective amount of (E)-3-[2-n-butyl-1-{(4-carboxynaphth-1-yl)methyl}-1H-imidazol-5-yl]-2-(2-thienyl)methyl-2-propenoic acid.

* * * * *